(12) United States Patent
Westby et al.

(10) Patent No.: US 12,138,292 B2
(45) Date of Patent: Nov. 12, 2024

(54) COMPOUNDS AND THERAPEUTICS USES THEREOF

(71) Applicant: Centauri Therapeutics Limited (GB/GB), London (GB)

(72) Inventors: Michael Westby, Sandwich (GB); Melanie Glossop, Sandwich (GB); Christine Watson, Sandwich (GB)

(73) Assignee: Centauri Therapeutics Limited (GB/GB), London (GB)

( * ) Notice: Subject to any disclaimer, the term of this patent is extended or adjusted under 35 U.S.C. 154(b) by 107 days.

(21) Appl. No.: 17/839,026

(22) Filed: Jun. 13, 2022

(65) Prior Publication Data

US 2022/0313776 A1 Oct. 6, 2022

Related U.S. Application Data

(62) Division of application No. 16/610,741, filed as application No. PCT/GB2018/051213 on May 4, 2018, now Pat. No. 11,406,683.

(30) Foreign Application Priority Data

May 4, 2017 (GB) .................................... 1707079

(51) Int. Cl.
| | |
|---|---|
| *A61K 38/12* | (2006.01) |
| *A61K 31/7004* | (2006.01) |
| *A61K 47/54* | (2017.01) |
| *A61K 47/64* | (2017.01) |
| *A61P 31/04* | (2006.01) |

(52) U.S. Cl.
CPC .......... *A61K 38/12* (2013.01); *A61K 31/7004* (2013.01); *A61K 47/549* (2017.08); *A61K 47/64* (2017.08); *A61P 31/04* (2018.01)

(58) Field of Classification Search
None
See application file for complete search history.

(56) References Cited

U.S. PATENT DOCUMENTS

| | | |
|---|---|---|
| 2008/0287345 A1 | 11/2008 | Vaara et al. |
| 2013/0149331 A1 | 6/2013 | Wang et al. |
| 2014/0112975 A1 | 4/2014 | Kiessling et al. |

FOREIGN PATENT DOCUMENTS

| | | |
|---|---|---|
| WO | 2017060728 A1 | 4/2017 |
| WO | 2017060729 A1 | 4/2017 |
| WO | 2018006063 A1 | 1/2018 |

OTHER PUBLICATIONS

Bucklin S E et al, "Therapeutic Efficacy of a Polymyxin B-Dextran 70 Conjugate in Experimental Model of Endotoxemia", Antimicrobial Agents and Chemotherapy, American Society for Microbiology, US, vol. 39, No. 7, Jul. 1, 1995.
International Search Report, Nov. 7, 2018.

*Primary Examiner* — Sudhakar Katakam
*Assistant Examiner* — Zachary J Miknis
(74) *Attorney, Agent, or Firm* — Aura IP Law, PC

(57) ABSTRACT

The invention relates to novel compounds with the ability to link an immune response to a pathogen, to the use of said compounds in a disease or disorder mediated and/or caused by an infective agent, to compositions containing said compounds, processes for their preparation and to novel intermediates used in said process.

1 Claim, 8 Drawing Sheets

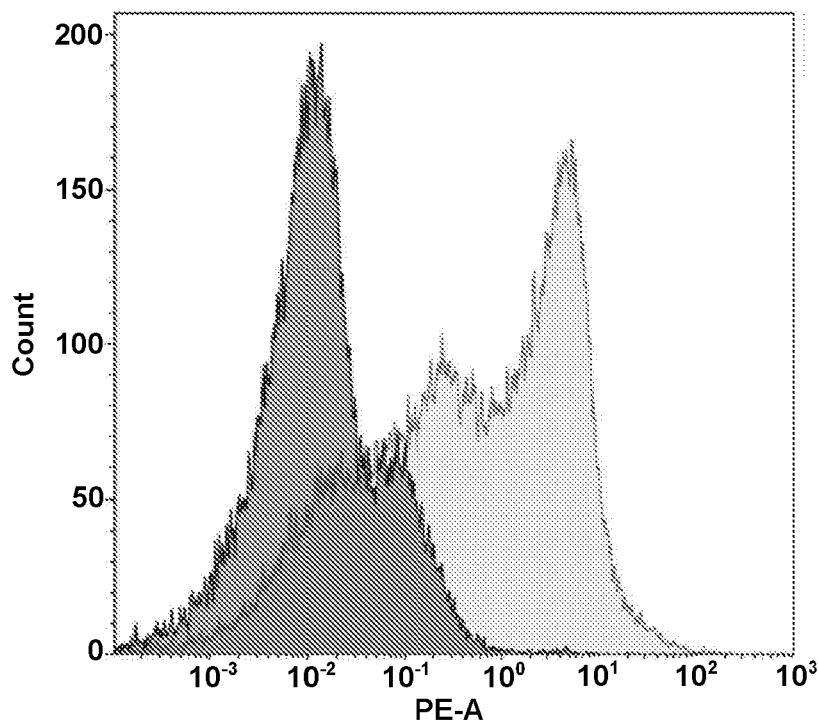
Example 3 (40µM)
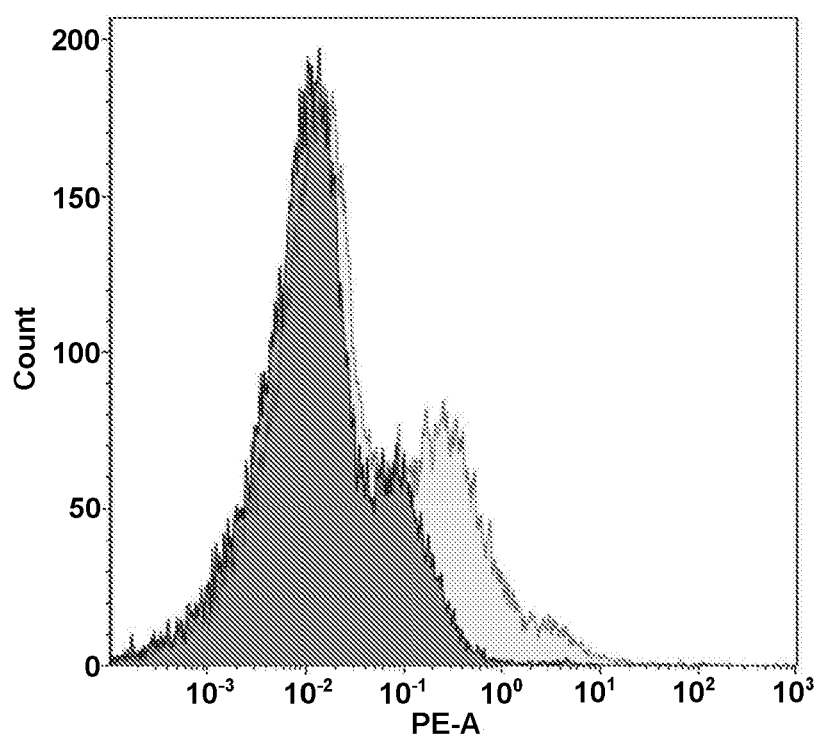
Example 4 (40µM)
FIGURE 1 (ctd.)

Example 5 (40µM)
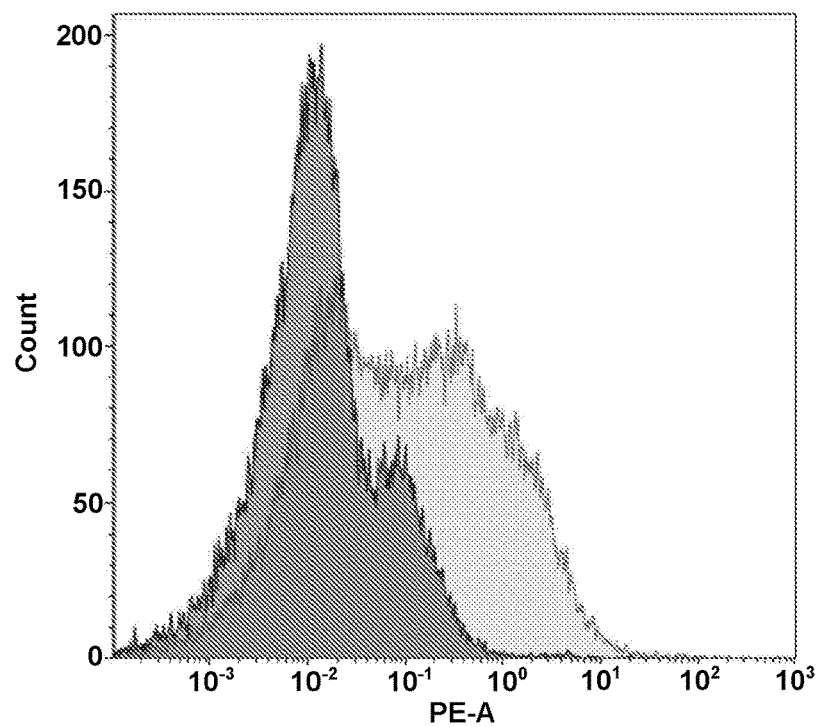
Example 6 (40µM)
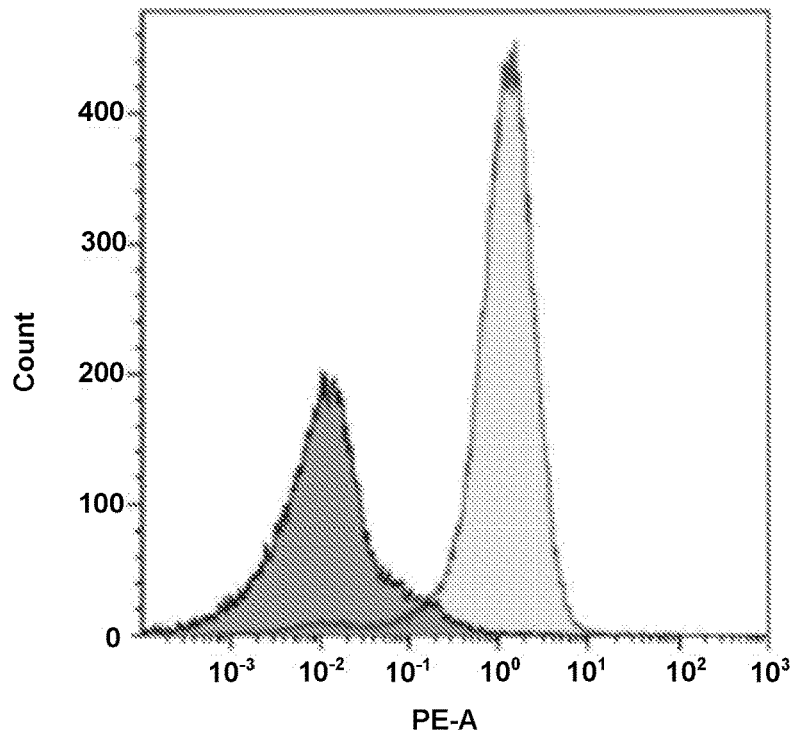
FIGURE 1 (ctd.)

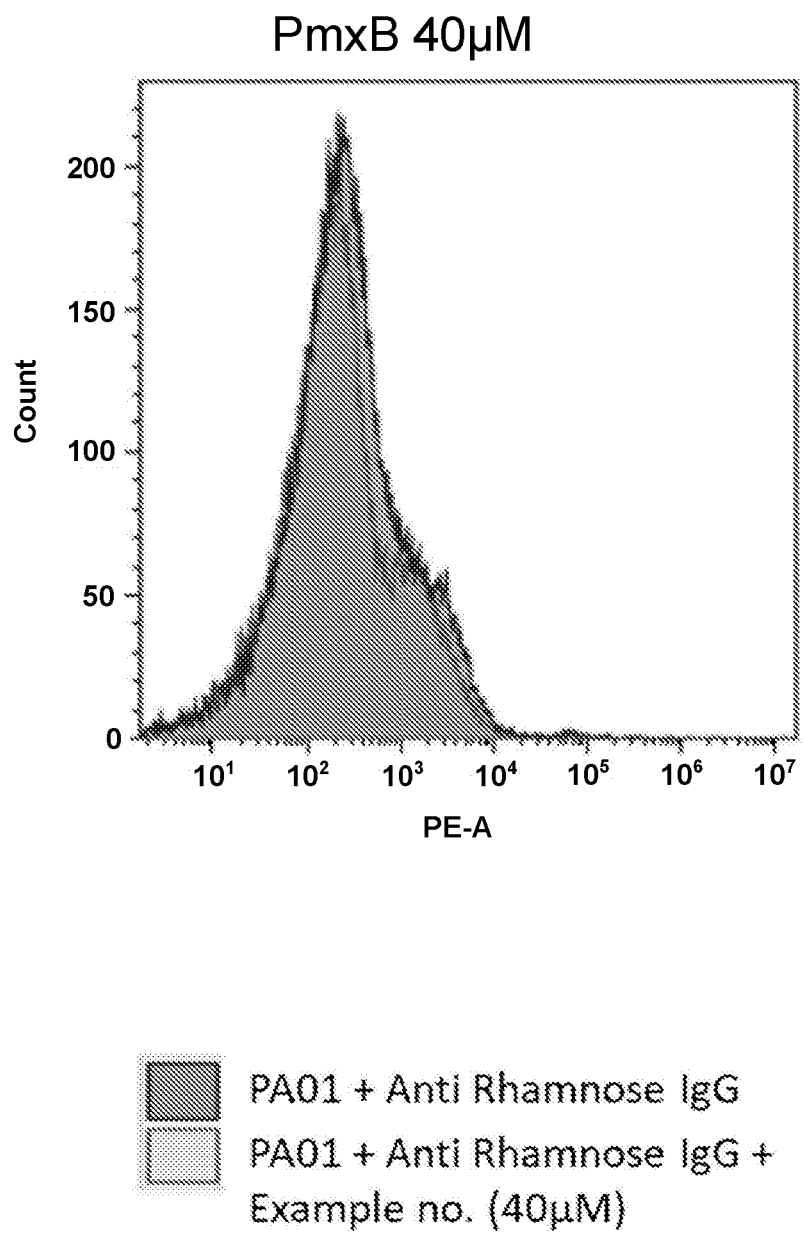
FIGURE 1 (ctd.)

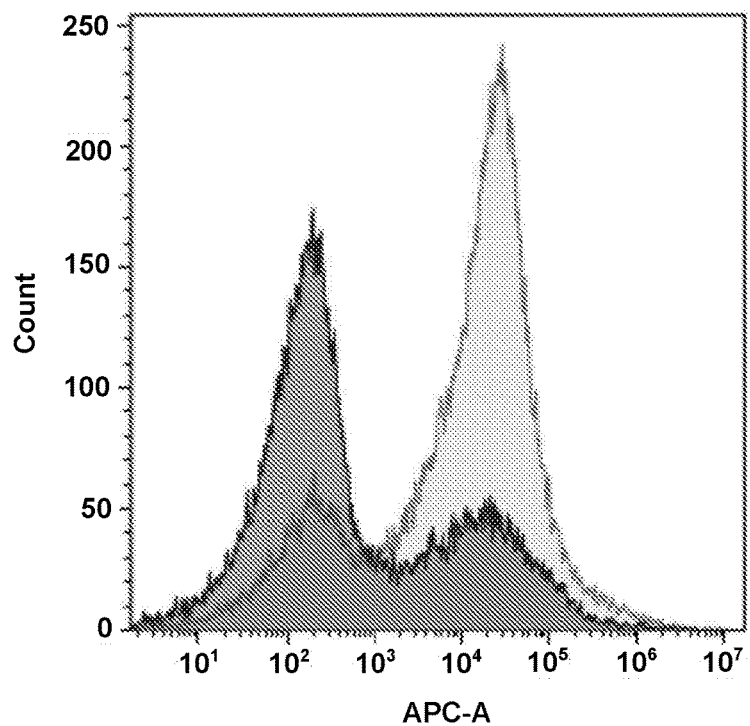
Example 3 (5μM)
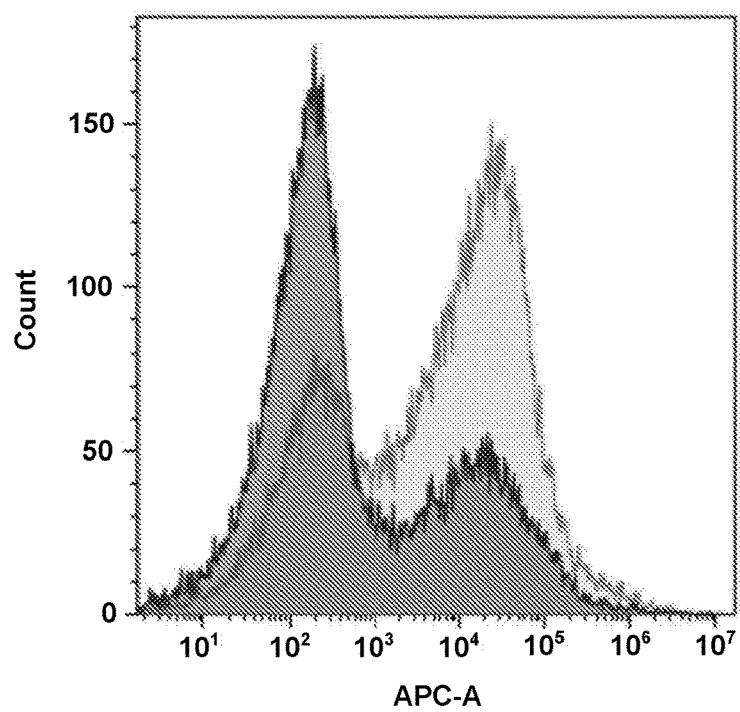
Example 4 (5μM)
FIGURE 2 (ctd.)

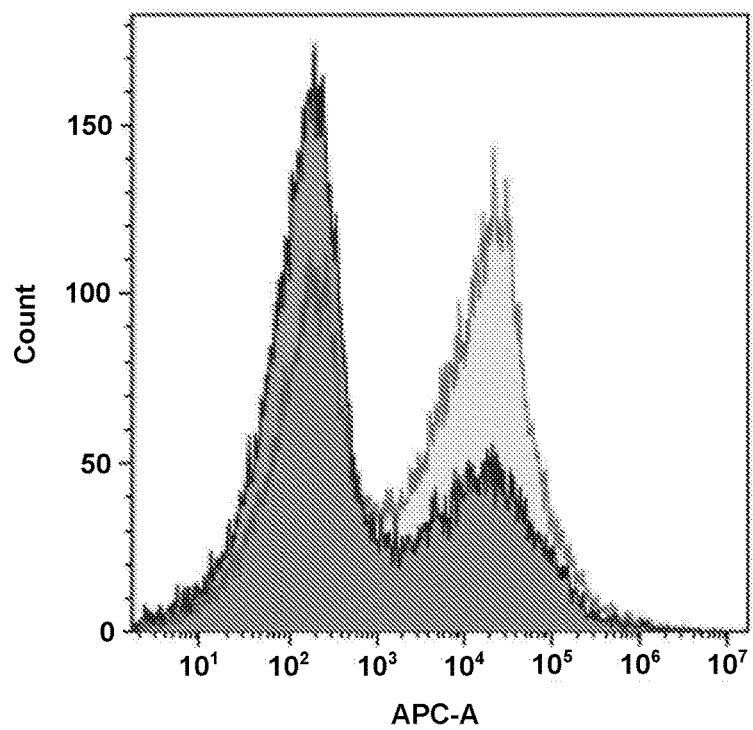
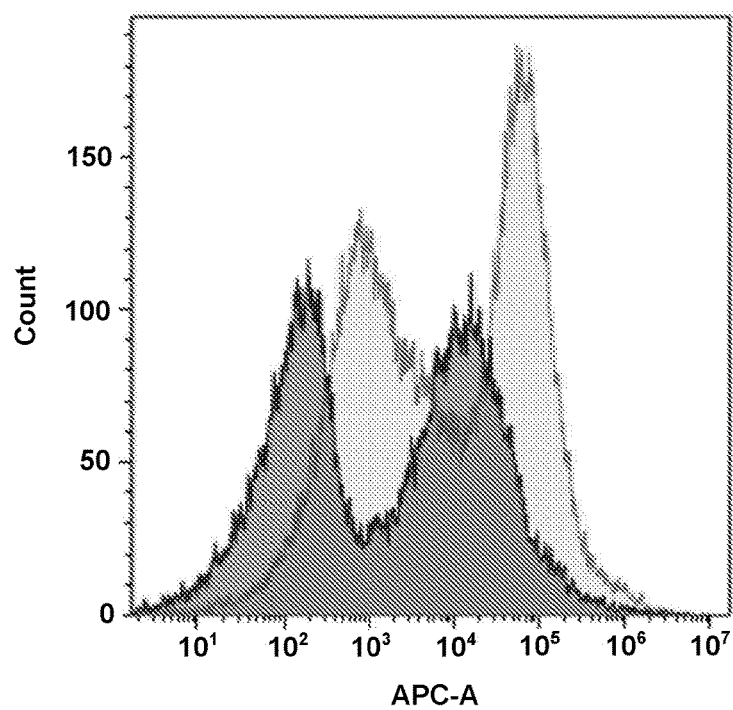
FIGURE 2 (ctd.)

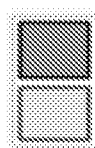 E.Coli K1 + 25% serum
E.Coli K1 + 25% serum + Example no. (5 µM)
FIGURE 2 (ctd.)

COMPOUNDS AND THERAPEUTICS USES THEREOF

CROSS-REFERENCE TO RELATED APPLICATIONS

This application claims priority as a divisional application under 35 U.S.C. § 121 to U.S. application Ser. No. 16/610,741, entitled "NOVEL COMPOUNDS AND THERAPEUTICS USES THEREOF." filed on Nov. 4, 2019, which is a U.S. National Stage entry under 35 U.S.C. § 371 of International Application No. PCT/GB2018/051213 filed on May 4, 2018, designating the United States of America and published in English on Nov. 8, 2018, which in turn claims priority to Great Britain Patent Application No. 1707079.8 filed on May 4, 2017, each of which is hereby incorporated by reference in its entirety.

FIELD OF THE INVENTION

The invention relates to novel compounds with the ability to link an immune response to a pathogen, to the use of said compounds in a disease or disorder mediated and/or caused by an infective agent, to compositions containing said compounds, processes for their preparation and to novel intermediates used in said process.

BACKGROUND OF THE INVENTION

There is a need to find novel ways to recruit an individual's immune system to fight disease. The human immune system continually surveys the body seeking foreign signals to identify potentially harmful pathogens or mutated human cells (that could become a cause of cancerous growth) and target them for elimination. Natural antibodies exist that can be recruited to said pathogens or mutated human cells to drive the immune system to eliminate the threat. The invention details the use of a novel set of linker molecules that are designed to attract these natural antibodies in such a way as to be able to maximise the efficacy of immune recruitment while minimising potential side effects.

There is an urgent need to identify novel ways of treating bacterial, viral and fungal infections. Drug resistance is becoming a major global health threat. For example, more than 2 million people in the US were infected with bacteria resistant to at least one class of antibiotics (Centers for Disease Control and Prevention, 2013). Overall, the identification of new antibiotics targeting resistant strains of gram-negative organisms has been particularly difficult, in part due to the complex and evolving strategy these bacteria use to prevent antibiotic action (e.g., production of antibiotic inactivating enzymes, ability to transfer of resistance between strains, efflux pumps to prevent intracellular action) coupled with their naturally impermeable cell membranes that make it hard to identify drugs that penetrate into the cell and inhibit key targets. Further, many strains utilize multiple resistance mechanisms making it difficult for a single antibiotic to overcome.

An innovative approach to the treatment of infectious disease was disclosed in WO 01/45734 which describes a set of novel immunity linkers. Examples of said linker moieties include compounds or agents which are recognised by the immune system of said individual as foreign and which would therefore trigger an immune response. One such example is a carbohydrate molecule capable of binding to a human anti-alpha-galactosyl antibody (i.e. galactosyl-alpha-1,3-galactosyl-beta-1,4-N-acetylglucosamine) which results in redirection of the natural human serum antibody anti-alpha-galactosyl. The resultant effect of said immunity linker molecule is that the immune response of the individual is diverted from the pre-existing immune response of said individual towards the target, i.e. the pathogen.

Another such example is a carbohydrate molecule capable of binding to human serum antibodies such as anti-Rhamnose (i.e. L-Rhamnose) resulting in target cell destruction (Kiessling et al (2014) ChemBioChem 15(10), 1393-1398; US 2014/0112975; Li et al (2016) ACS Chem. Biology 11(5), 1205-1209).

There is therefore a need for alternative immunity linker molecules for the treatment of a disease or disorder mediated and/or caused by an infective agent.

SUMMARY OF THE INVENTION

According to a first aspect of the invention, there is provided a compound of formula (I) or a pharmaceutically acceptable salt thereof:

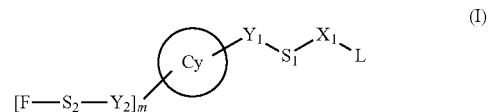

wherein:

L represents a binding moiety selected from a cationic anti-microbial peptide linked to $X_1$ by an amine;

$S_1$ represents a bond or a spacer selected from a $-(CH_2)_a-$ or $-(CH_2)_b-(CH_2-CH_2-O)_c(CH_2)_d-$ group, wherein one or two of said $-CH_2-$ groups may optionally be substituted by a $-C(O)NH-$ or $-NHC(O)-$ group;

a represents an integer selected from 1 to 15;
b represents an integer selected from 0 to 5;
c represents an integer selected from 1 to 20;
d represents an integer selected from 1 to 5;

$S_2$ represents a spacer selected from a $-(CH_2)_e-$ or $-(CH_2)_f-(CH_2-CH_2-O)_g-(CH_2)_h-$ group, wherein one or two of said $-CH_2-$ groups may optionally be substituted by a $-C(O)NH-$ or $-NHC(O)-$ group;

e represents an integer selected from 1 to 15;
f represents an integer selected from 1 to 10;
g represents an integer selected from 1 to 15;
h represents an integer selected from 1 to 5;

$X_1$ represents a bond or $-O(O)-$;

$Y_1$ and $Y_2$ independently represent a bond, $-O-$, $-S-$, $-NH-$, $-C(O)-$, $-NHC(O)-$ or $-C(O)NH-$ group;

F represents Rhamnose;

m represents an integer selected from 1 to 5; and

Cy represents phenyl, biphenyl or triphenyl, such that when Cy represents biphenyl or triphenyl, said $-Y_1-S_1-X_1-L$ group may be present on any of said phenyl rings and said $[F-S_2-Y_2]_m-$ group or groups may be present on any of said phenyl rings.

DETAILED DESCRIPTION OF THE INVENTION

Figure 1:
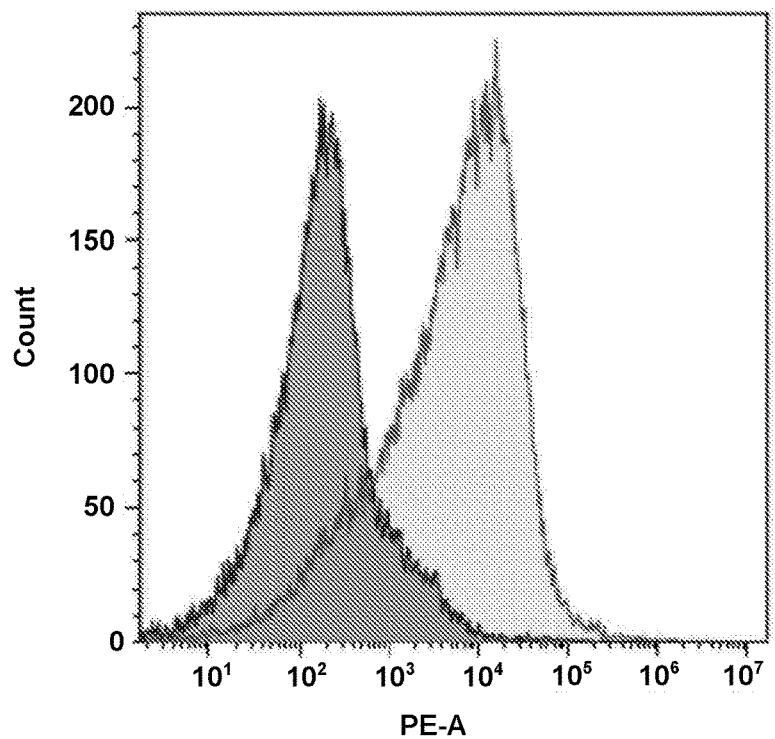
FIG. 1: Binding of anti-Rhamnose IgG antibodies to the surface of the bacteria in the presence and absence of the respective compounds using the flow cytometry assay described herein.
Figure 1:
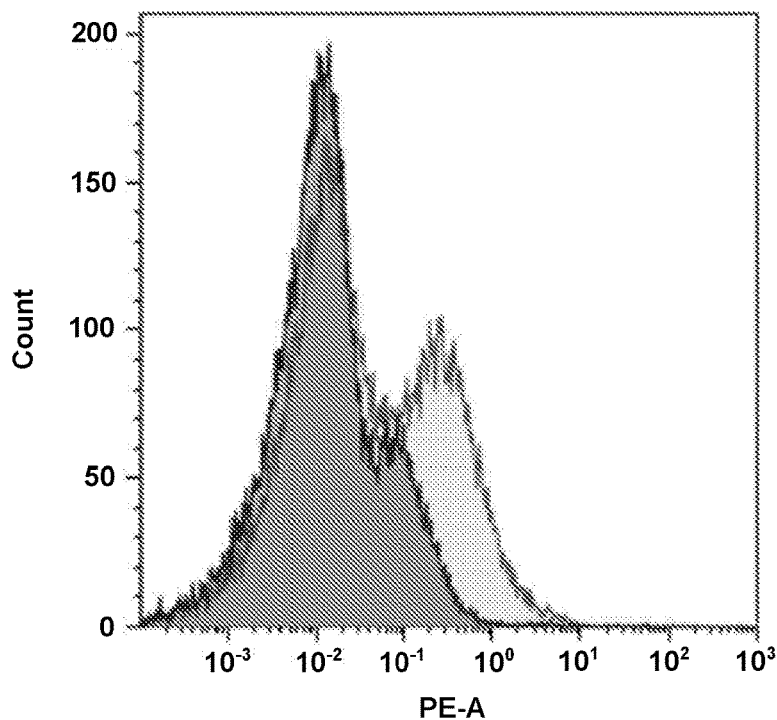

The invention comprises a conjugate of a cationic peptide (that is shown to specifically bind to bacteria) and the one or more Rhamnose units connected via a linker. An example of a cationic peptide is polymyxin B (or polymyxin nonapeptide, colistin or a derivative thereof). This family of cationic peptides bind to lipid A on the bacterial cell surface and, when conjugated to Rhamnose linkers, will present Rhamnose, resulting in anti-Rhamnose antibody (anti-Rha) recruitment and cell killing. Resistance rates are likely to be low as lipid A is important in the survival of gram-negative bacteria. In fact, even polymyxin-resistant strains retain binding sites for cationic peptides and as such the peptide-Rhamnose conjugate. Thus, the invention may retain, or have improved, efficacy against these strains.

Clearly, new innovative therapies that work through novel mechanisms, and are not impacted by antibiotic resistance mechanisms, are particularly attractive. The solution provided by the invention, i.e. the combination of the broad spectrum bacterial binding capability of a cationic peptide with the unique ability to specifically recruit naturally occurring anti-Rha antibodies to the bacterial surface, and redirect these antibodies to promote complement activation, phagocytosis and killing is very attractive. The invention has the potential to provide a novel therapy for bacterial infections with broad-spectrum activity. Efficacy that is independent of antibiotic resistance mechanisms has the potential to be effective against multi-drug resistant strains. The invention may work as a single agent as well as with standard-of-care treatment to reduce the dose and duration of therapy.

In one embodiment, $S_1$ represents a bond or a spacer selected from $—(CH_2)_a—$, wherein one or two of said $—CH_2—$ groups are optionally substituted by a $—C(O)NH—$ or $—NHC(O)—$ group (such as $—(CH_2)_5—CONH—(CH_2)_5$, $—(CH_2)_2—$, $—CH_2—CONH—(CH_2)_2—$, $—CH_2—NHCO—(CH_2)_4—CONH—(CH_2)_2—$ or $—(CH_2)_6—$) or $—(CH_2)_b—(CH_2—CH_2—O)_c—(CH_2)_d—$, wherein one or two of said $—CH_2—$ groups are optionally substituted by a $—C(O)NH—$ or $—NHC(O)—$ group (such as $—(CH_2CH_2O)_8—(CH_2)_2—$).

In a further embodiment, $S_1$ represents a bond or a spacer selected from $—(CH_2)_a—$, wherein one or two of said $—CH_2—$ groups are optionally substituted by a $—C(O)NH—$ or $—NHC(O)—$ group (such as $—(CH_2)_5—CONH—(CH_2)_5$) or $—(CH_2)_b—(CH_2—CH_2—O)_c—(CH_2)_d—$, wherein one or two of said $—CH_2—$ groups are optionally substituted by a $—C(O)NH—$ or $—NHC(O)—$ group (such as $—(CH_2CH_2O)_8—(CH_2)_2—$).

In a yet further embodiment, $S_1$ represents a spacer selected from:
$—(CH_2)_a—$, wherein one or two of said $—CH_2—$ groups are optionally substituted by a $—C(O)NH—$ or $—NHC(O)—$ group (such as $—(CH_2)_5—CONH—(CH_2)_5$); or
$—(CH_2)_b—(CH_2—CH_2—O)_c—(CH_2)_d—$, wherein one or two of said $—CH_2—$ groups are optionally substituted by a $—C(O)NH—$ or $—NHC(O)—$ group (such as $—(CH_2CH_2O)_8—(CH_2)_2—$).

It will be appreciated that a, b, c, d, e, f, g and h are selected to maintain a suitable linker length between groups F and L. Examples of suitable linker lengths between F and L range from about 5 Å to about 50 Å or more in length, about 6 Å to about 45 Å, about 7 Å to about 40 Å, about 8 Å to about 35 Å, about 9 Å to about 30 Å, about 10 Å to about 25 Å, about 11 Å to about 20 Å, about 12 Å to about 15 Å. Thus, in one embodiment, a, b, c, d, e, f, g and h represent a total integer of no more than 30, such as between 5 and 30, such as between 7 and 29.

In one embodiment, a represents an integer selected from 1 to 10. In a further embodiment, a represents an integer selected from 2 to 13. In a yet further embodiment, a represents an integer selected from 2, 4, 6, 9 or 11. In a still yet further embodiment, a represents an integer selected from 11.

In one embodiment, b represents an integer selected from 0 to 3. In a further embodiment, b represents an integer selected from 0, 2 or 3. In a yet further embodiment, b represents an integer selected from 0.

In one embodiment, c represents an integer selected from 1 to 15. In a further embodiment, c represents an integer selected from 1 to 12. In a yet further embodiment, c represents an integer selected from 1 to 10. In a yet further embodiment, c represents an integer selected from 8.

In one embodiment, d represents an integer selected from 1 to 3. In a further embodiment, d represents an integer selected from 1 or 2. In a yet further embodiment, d represents an integer selected from 2.

In one embodiment, $Y_1$ represents $—C(O)NH—$ or $—C(O)—$. In a further embodiment, $Y_1$ represents $—C(O)NH—$.

In one embodiment, $S_2$ represents a spacer selected from:
$—(CH_2)_e—$, wherein one or two of said $—CH_2—$ groups are optionally substituted by a $—C(O)NH—$ or $—NHC(O)—$ group (such as $—(CH_2)_3—NHCO—CH_2—$, $—(CH_2)_3—NHCO—$, $—(CH_2)_3—$, $—(CH_2)_3—NHCO—(CH_2)_4—CONH—CH_2—$, $—(CH_2)_3—NH—CH_2—$ or $—(CH_2)_3—CONH—(CH_2)_2—NHCO—CH_2—$); or
$—(CH_2)_f—(CH_2—CH_2—O)_g—(CH_2)_h—$, wherein one or two of said $—CH_2—$ groups are optionally substituted by a $—C(O)NH—$ or $—NHC(O)—$ group (such as $—(CH_2)_3—NHCO—(CH_2)_2—(OCH_2CH_2)_4—NHCO—CH_2—$, $—(CH_2)_4—NHCO—(CH_2)_2—(OCH_2CH_2)_4—NHCO—CH_2—$ or $—(CH_2)_3—CONH—(CH_2CH_2O)_4—(CH_2)_2—NHCO—(CH_2)—$).

In a further embodiment, $S_2$ represents a spacer selected from:
$—(CH_2)_e—$, wherein one or two of said $—CH_2—$ groups are optionally substituted by a $—C(O)NH—$ or $—NHC(O)—$ group (such as $—(CH_2)_3—NHCO—CH_2—$, $—(CH_2)_3—NHCO—$, $—(CH_2)_3—$, $—(CH_2)_3—NHCO—(CH_2)_4—CONH—CH_2—$ or $—(CH_2)_3—NH—CH_2—$); or
$—(CH_2)_f—(CH_2—CH_2—O)_g—(CH_2)_h—$, wherein one or two of said $—CH_2—$ groups are optionally substituted by a $—C(O)NH—$ or $—NHC(O)—$ group (such as $—(CH_2)_3—NHCO—(CH_2)_2—(OCH_2CH_2)_4—NHCO—CH_2—$ or $—(CH_2)_4—NHCO—(CH_2)_2—(OCH_2CH_2)_4—NHCO—CH_2—$).

In a further embodiment, $S_2$ represents a spacer selected from:
$—(CH_2)_e—$, wherein one or two of said $—CH_2—$ groups are optionally substituted by a $—C(O)NH—$ or $—NHC(O)—$ group (such as $—(CH_2)_3—NHCO—CH_2—$, $—(CH_2)_3—NHCO—$, $—(CH_2)_3—$, $—(CH_2)_3—NHCO—(CH_2)_4—CONH—CH_2—$ or $—(CH_2)_3—NH—CH_2—$); or
$—(CH_2)_f—(CH_2—CH_2—O)_g—(CH_2)_h—$, wherein one or two of said $—CH_2—$ groups are optionally substituted by a $—C(O)NH—$ or $—NHC(O)—$ group (such as $—(CH_2)_3—NHCO—(CH_2)_2—(OCH_2CH_2)_4—NHCO—CH_2—$ or $—(CH_2)_4—NHCO—(CH_2)_2—(OCH_2CH_2)_4—NHCO—CH_2—$).

In a yet further embodiment, $S_2$ represents a spacer selected from:

—$(CH_2)_e$—, wherein one or two of said —$CH_2$— groups are optionally substituted by a —C(O)NH— or —NHC(O)— group (such as —$(CH_2)_3$—CONH—$(CH_2)_2$—NHCO—$CH_2$—); or —$(CH_2)_f$—$(CH_2$—$CH_2$—$O)_g$—$(CH_2)_h$—, wherein one or two of said —$CH_2$— groups are optionally substituted by a —C(O)NH— or —NHC(O)— group (such as —$(CH_2)_3$—CONH—$(CH_2CH_2O)_4$—$(CH_2)_2$—NHCO—$(CH_2)$—).

In one embodiment, e represents an integer selected from 1 to 10. In a further embodiment, e represents an integer selected from 4 to 10. In a yet further embodiment, e represents an integer selected from 4, 5, 8 or 10. In a yet further embodiment, e represents an integer selected from 4, 5 or 10. In a still yet further embodiment, e represents an integer selected from 5. In a still yet further embodiment, e represents an integer selected from 8.

In one embodiment, f represents an integer selected from 1 to 8. In a further embodiment, f represents an integer selected from 2 to 6. In a yet further embodiment, f represents an integer selected from 6. In a yet further embodiment, f represents an integer selected from 4.

In one embodiment, g represents an integer selected from 1 to 5. In a further embodiment, g represents an integer selected from 1 to 4. In a yet further embodiment, g represents an integer selected from 4.

In one embodiment, h represents an integer selected from 1 to 4. In a further embodiment, h represents an integer selected from 1 to 3. In a further embodiment, h represents an integer selected from 1 or 2. In a yet further embodiment, h represents an integer selected from 2. In a yet further embodiment, h represents an integer selected from 4.

In one embodiment, $Y_2$ represents —O—.

In one embodiment, m represents an integer selected from 1 to 4. In a further embodiment, m represents an integer selected from 1 to 3. In a yet further embodiment, m represents an integer selected from 1 or 3.

In one embodiment, Cy represents phenyl or biphenyl. In a further embodiment, Cy represents biphenyl.

In one embodiment, $X_1$ represents —C(O)—.

References herein to the term "Rhamnose" include (2R,3R,4R,5R,6S)-6-Methyloxane-2,3,4,5-tetrol (also known as isodulcit, α-L-Rhamnose, L-Rhamnose, L-Mannomethylose, α-L-Rha, α-L-Rhamnoside, α-L-Mannomethylose, 6-Deoxy-L-mannose, Rhamnopyranose and Rhamnopyranoside). Rhamnose (Rha, Rham) is a naturally occurring deoxy sugar. It can be classified as either a methyl-pentose or a 6-deoxy-hexose. Rhamnose occurs in nature in its L-form as L-rhamnose (6-deoxy-L-mannose). In one embodiment, F is selected from L-Rhamnose. L-Rhamnose is an L-configured, deoxy-sugar monosaccharide capable of binding to and recruiting anti-L-Rha antibodies found in human sera.

In one particular embodiment, F has a structure as shown in one of the following formulae:

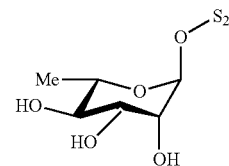

wherein $S_2$ refers to the point of attachment to the $S_2$ group.

References herein to the term "binding moiety" refer to any suitable moiety which is capable of binding to a further component. The invention requires the binding moiety to be a cationic anti-microbial peptide linked to $X_1$ by an amine.

In one embodiment, L represents a lipopeptide. In a further embodiment, the lipopeptide comprises polymyxin or a derivative thereof. Examples of suitable polymyxin and derivatives thereof are described in Velkov et al (2016) Future Med Chem 8(10), 1017-1025, the polymyxins and derivatives thereof are herein incorporated by reference. In one embodiment, the polymyxin or a derivative thereof is selected from Polymyxin B, Polymyxin $B_2$, Polymyxin Nonapeptide, Colistin A, Colistin B, CB-182,204 (Cubist Pharmaceuticals), 5a (Pfizer), 5× (Pfizer), CA 14 (Cantab Anti-Infectives) CA824 (Cantab Anti-Infectives), NAB739 (Northern Antibiotics), NAB741 (Northern Antibiotics), NAB7061 (Northern Antibiotics), 38 (University of Queensland), FADDI-002 (Monash University), FADDI-100 (Monash University), or derivatives thereof. In a further embodiment, the polymyxin is Polymyxin B or derivative which has the following structure:

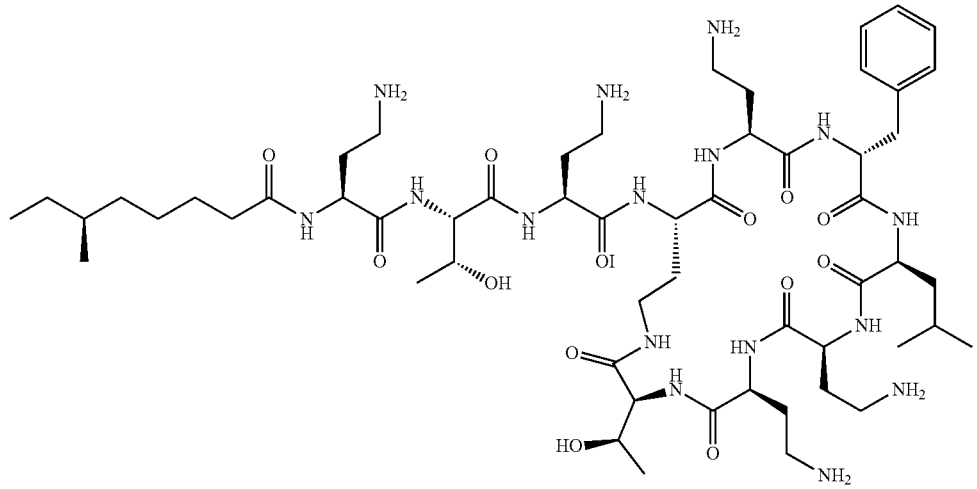

In a yet further embodiment, the Polymyxin B derivative comprises the following structures (where the point of attachment with $X_1$ is shown):
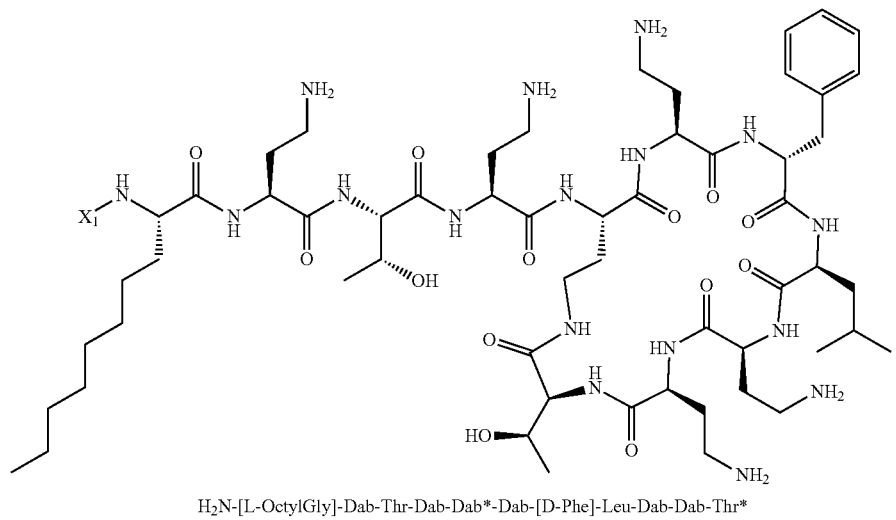
H₂N-[L-OctylGly]-Dab-Thr-Dab-Dab*-Dab-[D-Phe]-Leu-Dab-Dab-Thr*
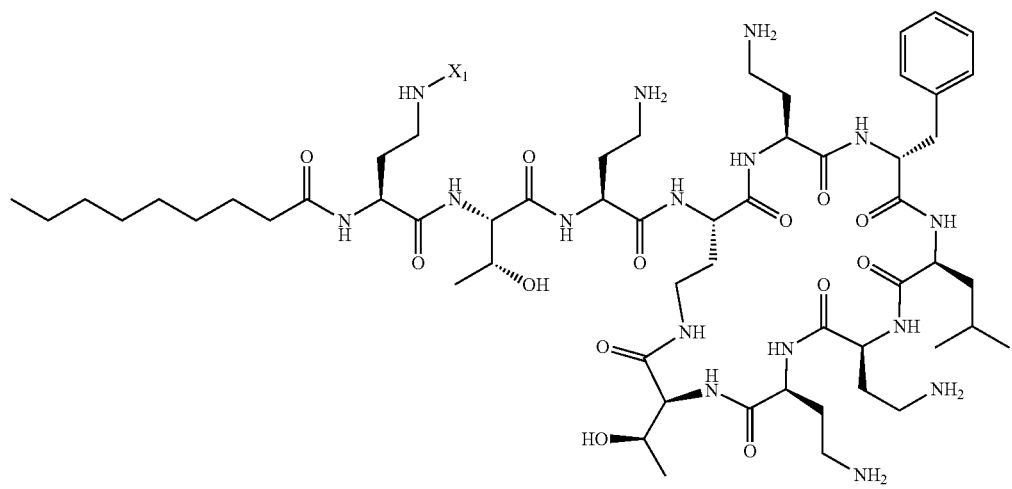
Nonanamide-Dab(NH₂)-Thr-Dab-Dab*-Dab-[D-Phe]-Leu-Dab-Dab-Thr*
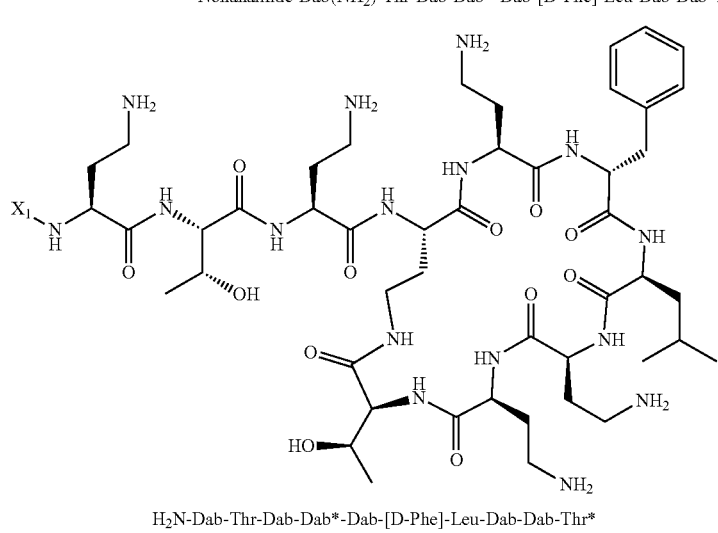
H₂N-Dab-Thr-Dab-Dab*-Dab-[D-Phe]-Leu-Dab-Dab-Thr*

-continued
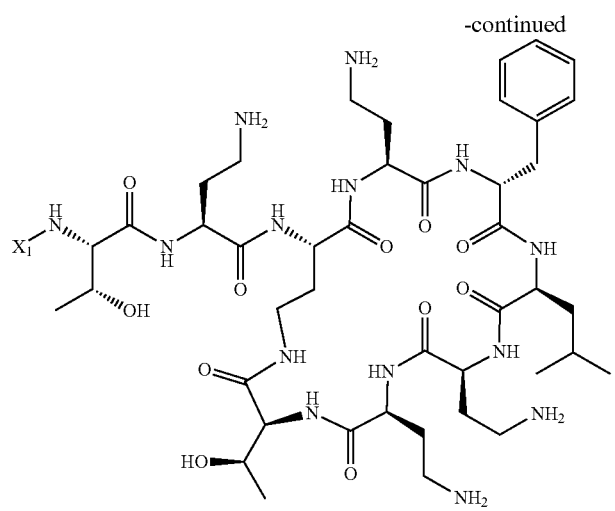
H₂N-Thr-Dab-Dab*-Dab-[D-Phe]-Leu-Dab-Dab-Thr*
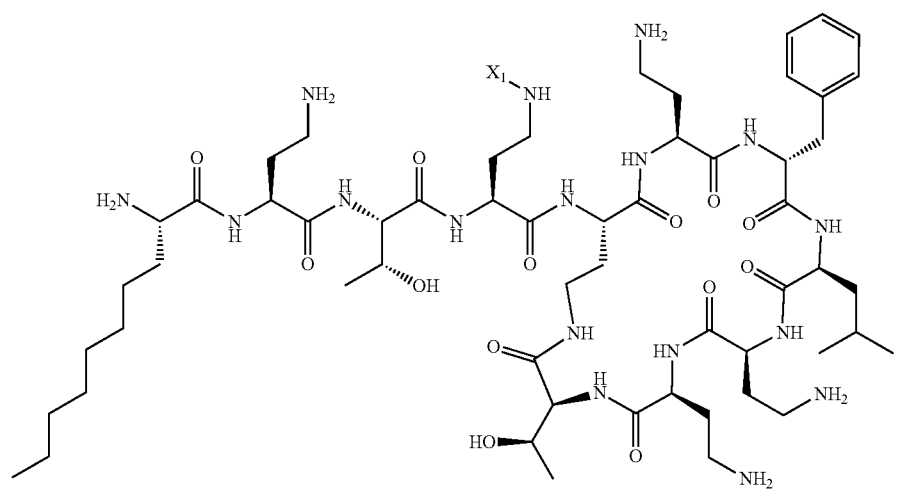
H₂N-[L-OctylGly]-Dab-Thr-Dab(NH₂)-Dab*-Dab-[D-Phe]-Leu-Dab-Dab-Thr*
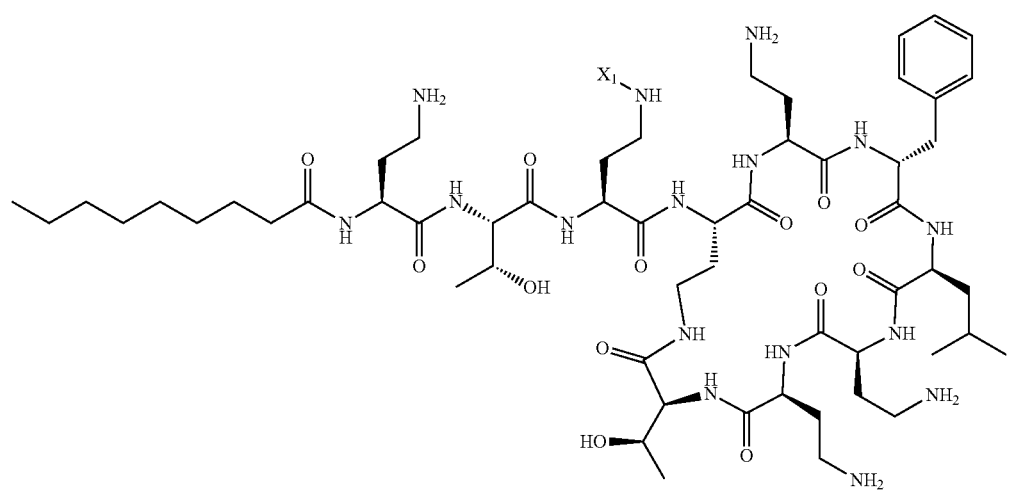
Nonanamide-Dab-Thr-Dab(NH₂)-Dab*-Dab-[D-Phe]-Leu-Dab-Dab-Thr*

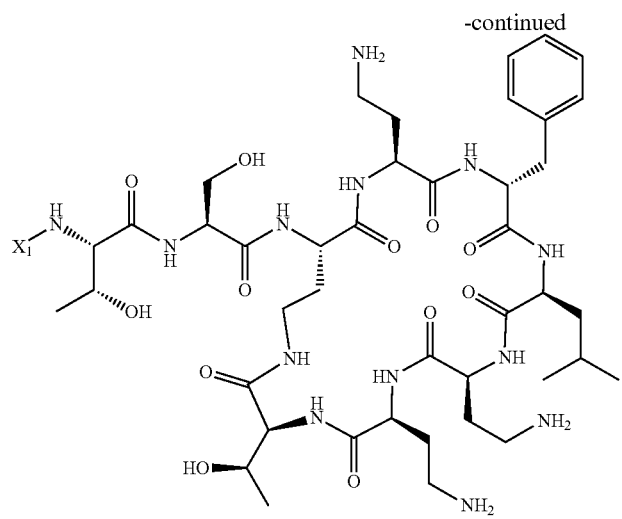
H₂N-Thr-Ser-Dab*-Dab-[D-Phe]-Leu-Dab-Dab-Thr*
In a still yet further embodiment, the Polymyxin B derivative comprises the following structures (where the point of attachment with $X_1$ is shown):
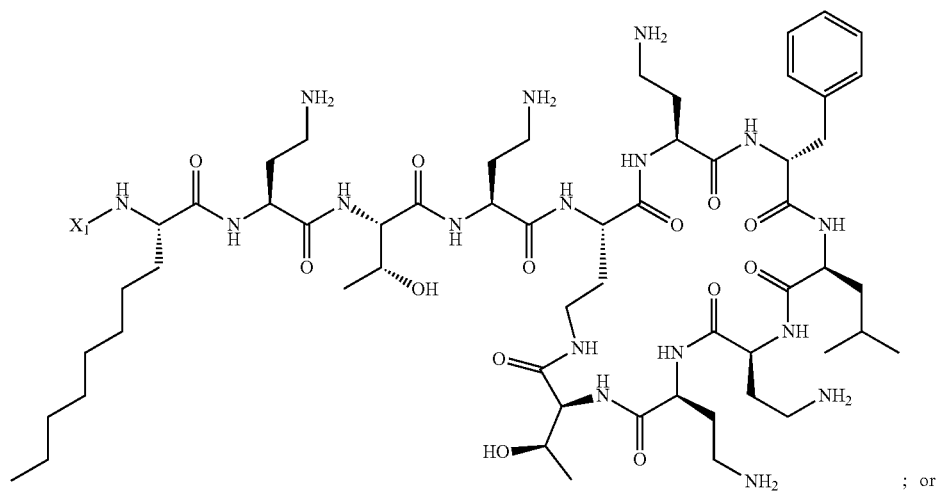
H₂N-[L-OctylGly]-Dab-Thr-Dab-Dab*-Dab-[D-Phe]-Leu-Dab-Dab-Thr*
; or

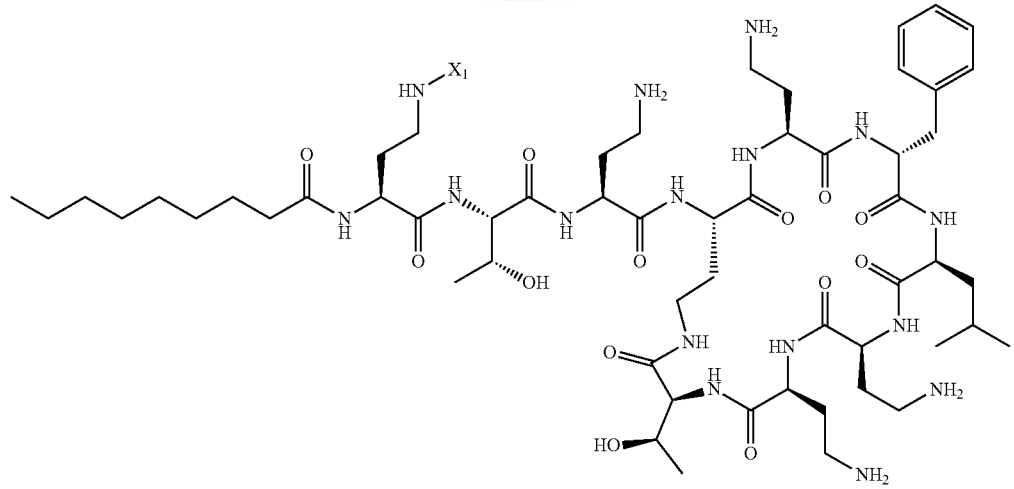

Nonanamide-Dab(NH$_2$)-Thr-Dab-Dab*-Dab-[D-Phe]-Leu-Dab-Dab-Thr*

It will be appreciated that the cationic anti-microbial peptides of the present invention will be configured to bind to a specific pathogen or infective agent.

In one embodiment, the invention provides a compound of formula (I) which comprises a compound of Examples 1-11 or a pharmaceutically acceptable salt thereof. In one embodiment, the invention provides a compound of formula (I) which is the free base or the trifluoroacetate salt of a compound of Examples 1-11.

In one embodiment, the invention provides a compound of formula (I) which comprises a compound of Examples 1-10 or a pharmaceutically acceptable salt thereof. In one embodiment, the invention provides a compound of formula (I) which is the free base or the trifluoroacetate salt of a compound of Examples 1-10.

In one embodiment, the invention provides a compound of formula (I) which comprises a compound of Examples 1-6 or a pharmaceutically acceptable salt thereof. In one embodiment, the invention provides a compound of formula (I) which is the free base or the trifluoroacetate salt of a compound of Examples 1-6.

A reference to a compound of formula (I) and sub-groups thereof also includes ionic forms, salts, solvates, isomers (including geometric and stereochemical isomers), tautomers, N-oxides, esters, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, isotopes and protected forms thereof as defined in any aspect of the invention (except intermediate compounds in chemical processes) are referred to as "compounds of the invention".

Compounds of formula (I) can exist in the form of salts, for example acid addition salts or, in certain cases salts of organic and inorganic bases such as carboxylate, sulfonate and phosphate salts. All such salts are within the scope of this invention, and references to compounds of formula (I) include the salt forms of the compounds.

The salts of the present invention can be synthesized from the parent compound that contains a basic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt. Another particular salt is the hydrogensulfate salt, also known as a hemisulfate salt.

Where the compounds of formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention.

Compounds of formula (I) containing an amine function may also form N-oxides. A reference herein to a compound of formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Also included within the scope of the compound and various salts of the invention are polymorphs thereof.

Compounds of formula (I) may exist in a number of different geometric isomeric, and tautomeric forms and references to compounds of formula (I) include all such forms. For the avoidance of doubt, where a compound can exist in one of several geometric isomeric or tautomeric forms and only one is specifically described or shown, all others are nevertheless embraced by formula (I).

The present invention includes all pharmaceutically acceptable isotopically-labelled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, fluorine, such as $^{18}$F, nitrogen, such as $^{13}$N and $^{15}$N, oxygen, such as $^{15}$O, $^{17}$O and $^{18}$O.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labelled compounds of formula (I) can generally be prepared by conventional techniques known to those skilled in the art or by processes analogous to those described in the accompanying Examples and Preparations using appropriate isotopically-labelled reagents in place of the non-labelled reagent previously employed.

Methods for the Preparation of Compounds of Formula (I)

In this section, as in all other sections of this application unless the context indicates otherwise, references to formula (I) also include all other sub-groups and examples thereof as defined herein.

The compounds pertaining to the invention described herein may be prepared in a stepwise synthetic sequence as illustrated in the Schemes below. The syntheses involve the preparation of various central constructs (Cy) that enable choice of valency for F and choice of peptide for L within the molecule. Compounds of formula (I) can be prepared in accordance with synthetic methods well known to the skilled person. For example, one skilled in the art will appreciate that the chemical steps and choice of protecting groups may be managed in any order to enable synthetic success.

According to a further aspect of the invention there is provided a process for preparing a compound of formula (I) as hereinbefore defined which comprises:

(a) preparing a compound of formula (I) wherein $Y_1$ represents —CONH— (i.e. a compound of formula (IA)) by reacting a compound of formula (II) with a compound of formula (III) followed by a suitable deprotection step:

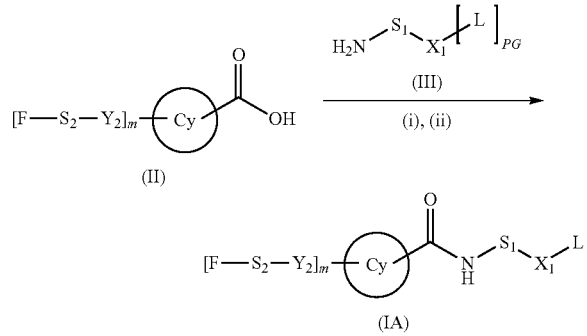

wherein $S_2$, $Y_2$, m, Cy, $S_1$, $X_1$, L and F are as defined hereinbefore and PG is a suitable peptide protecting group such as Dde or tertbutoxycarbonyl (Boc); or (b) preparing a compound of formula (I) wherein $Y_1$ represents —CONH— and $X_1$ represents —C(O)— (i.e. a compound of formula (IB)) by reacting a compound of formula (IV) with a compound of formula (V) followed by a suitable deprotection step:

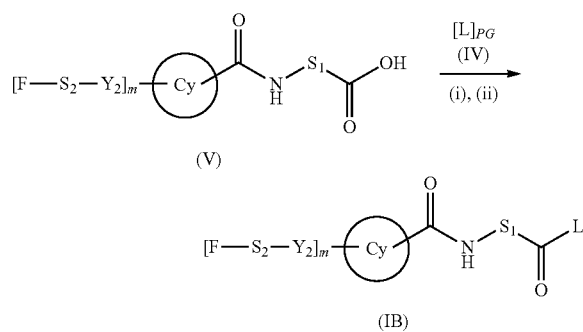

wherein $S_2$, $Y_2$, m, Cy, $S_1$, L and F are as defined hereinbefore and PG is a suitable peptide protecting group such as Dde or tertbutoxycarbonyl (Boc); or (c) preparing a compound of formula (I) by reacting a compound of formula (VI) with a compound of formula (VII) followed by a suitable deprotection step:

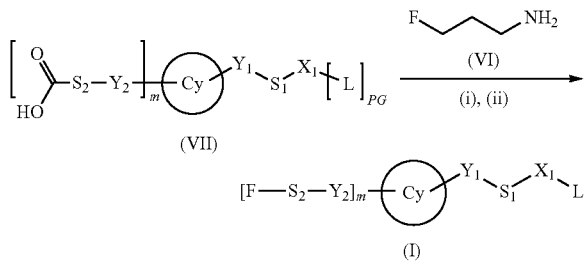

wherein $S_2$, $Y_2$, m, Cy, $S_1$, $X_1$, L and F are as defined hereinbefore (alternatively compounds of formula (VI) may consist of the formula F—$(CH_2)_3$—NHCO—$PEG_4$-$NH_2$), PG is a suitable peptide protecting group such as Dde or tertbutoxycarbonyl (Boc); or (d) interconversion of a compound of formula (I) or protected derivative thereof to a further compound of formula (I) or protected derivative thereof.

Step (i) in processes (a) to (c) typically comprise an amide bond formation reaction, which typically comprises activation of the carboxylic acid with either phosphate containing reagents, triazine based reagents or carbodiimide containing reagents in the presence of an organic base in an organic solvent. Preferred conditions comprise HATU ((1-[bis(dimethylamino)methylene]-1H-1,2,3-triazolo[4,5-b]pyridinium 3-oxidehexafluorophosphate) with diispropylethylamine in DMF.

Step (ii) in processes (a) to (c) typically comprise any suitable deprotection reaction, the conditions of which will depend upon the nature of the protecting group. When the protecting group comprises Dde, such a deprotection will typically comprise the use of hydrazine in DMF. When the protecting group comprises Cbz or benzyl, such a deprotection will typically comprise hydrogenation over a suitable catalyst such as palladium on carbon. When the protecting group comprises tertbutoxycarbonyl (Boc) or tert-butyl, such a deprotection will be acid mediated and will typically comprise TFA in DCM.

Process (d) typically comprises interconversion procedures known by one skilled in the art. For example, in compounds of formula (I), a first substituent may be converted by methods known by one skilled in the art into a second, alternative substituent. A wide range of well known functional group interconversions are known by a person skilled in the art for converting a precursor compound to a compound of formula (I) and are described in *Advanced Organic Chemistry* by Jerry March, 4th Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described in processes (a), (b), (c) and (d) are followed or preceded by one or more reactions known to the skilled in the art and are performed in an appropriate order to achieve the requisite substitutions on $S_2$, $Y_2$, m, Cy, $S_1$, $X_1$, $Y_1$, L and F defined above to afford other compounds of formula (I). Non-limiting examples of such reactions whose conditions can be found in the literature include:

protection of reactive functions,
deprotection of reactive functions,
halogenation,
dehalogenation,
dealkylation,
alkylation and arylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of ester groups,
amidification or transesterification of ester groups,
esterification or amidification of carboxylic groups,
halogen exchange,
nucleophilic substitution with amine, thiol or alcohol,
reductive amination, oxime formation on carbonyl and hydroxylamine groups, S-oxidation, N-oxidation, salification.

Compounds of formula (II) may be prepared according to the methods described in Scheme 1 from compounds of formula (VIII) and (VI) according to process steps (i) and (ii) as described hereinbefore (alternatively compounds of formula (VI) may consist of the formula F—(CH$_2$)$_3$—NHCO—PEG$_4$-NH$_2$).

Scheme 1

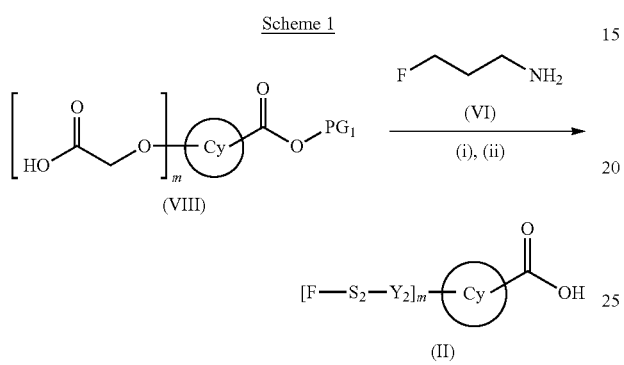

wherein m, Cy, Y$_2$, S$_2$ and F are as defined hereinbefore and PG$_1$ is a protecting group comprising benzyl.

Compounds of formula (II) may be prepared according to the methods described in Scheme 1A from compounds of formula (VIIIA) and (VIA) according to process steps (i) and (ii) as described hereinbefore.

Scheme 1A

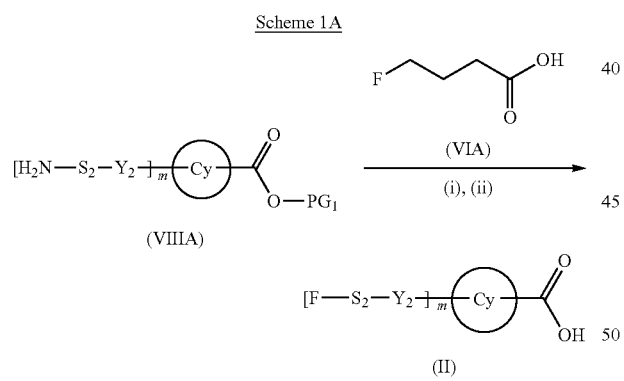

wherein m, Cy, Y$_2$, S$_2$ and F are as defined hereinbefore and PG$_1$ is a protecting group comprising benzyl.

Additionally, compounds of formula (V) may be prepared from compounds of formula (II) according to process steps (i) and (ii) as described hereinbefore with employment of a suitably chosen linker (S$_1$) comprising a suitable protecting group, such as benzyl, which is either commercially available or prepared as described in the literature by one skilled in the art.

Compounds of formula (VII) may be prepared according to the methods described in Scheme 2 from compounds of formula (III) and (IX) according to process steps (i) and (ii) as described hereinbefore.

Scheme 2

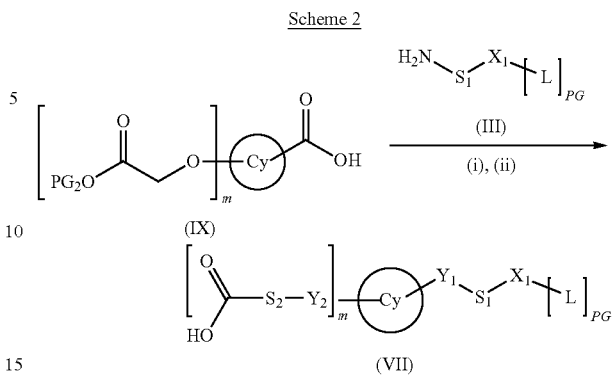

wherein m, Cy, Y$_2$, S$_1$, S$_2$, X$_1$ and F are as defined hereinbefore, Y$_1$ is —CONH—, PG$_2$ is a protecting group comprising tert-butyl and PG is a suitable peptide protecting group such as Dde or tertbutoxycarbonyl (Boc), Compounds of formula (VIII) may be prepared according to the methods described in Scheme 3 from compounds of formula (X) and (XI) according to process steps (iii) and (ii), an alkylation reaction followed by a deprotection reaction as described hereinbefore, respectively.

Scheme 3

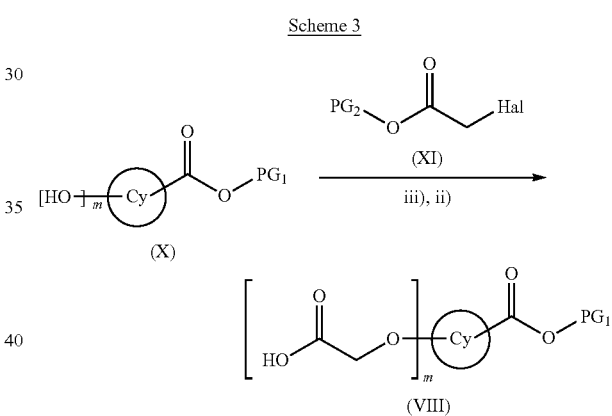

wherein m and Cy are as defined hereinbefore, PG$_2$ is a protecting group comprising tert-butyl, PG$_1$ is a protecting group comprising benzyl and Hal is a halide such as Cl, Br or I.

Step (iii) typically comprises alkylation conditions with compounds of formula (XI) in an inorganic base in a polar organic solvent at room temperature. Preferred conditions comprise potassium carbonate in DMF.

Similarly, compounds of formula (IX) may also be prepared according to Scheme 3 wherein alternative deprotection conditions may be employed. Following the alkylation step, wherein PG$_1$ is benzyl, PG$_1$ may be preferentially deprotected under hydrogenation conditions as previously described hereinbefore.

When Cy is bi-phenyl, compounds of formula (X) may be prepared by employment of a Suzuki reaction to construct the biphenyl unit. Preferred conditions comprise tetrakistriphenyl phosphine palladium (O) with sodium carbonate in dioxane and water at 100° C. When suitable required protecting groups are employed, such as TBS, such protecting groups may be deprotected using a fluoride mediated deprotection. Preferred conditions comprise TBAF in THF at room temperature.

Compounds of formula (VIIIA) may be prepared in accordance with Scheme 4 from compounds of formula (VIII) according to process steps (i) and (ii) as described hereinbefore.

Scheme 4

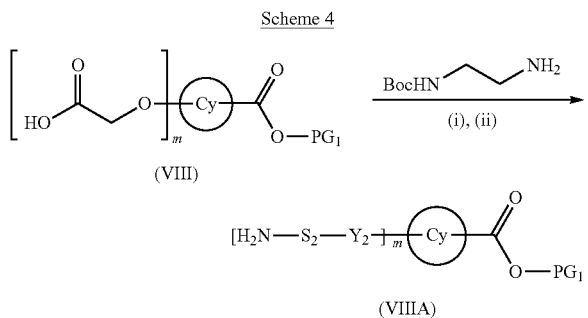

wherein m, Cy, $Y_2$ and $S_2$ are as defined hereinbefore and $PG_1$ is a protecting group comprising benzyl.

Compounds of formula (III), (IV), (VI) and (XI) are either commercially available, prepared according to the methods described herein or prepared according to the literature. Compounds of formula (VIA) may be prepared according to J. Am. Chem. Soc. (2010), 132, 17236-17246.

Pharmaceutical Compositions

While it is possible for the compound of formula (I) to be administered alone, it is preferable to present it as a pharmaceutical composition (e.g. formulation).

Thus, according to a further aspect, the invention provides a pharmaceutical composition, and methods of making a pharmaceutical composition comprising (e.g. admixing) at least one compound of the invention where L represents a cationic anti-microbial peptide, together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity (i.e. generally recognised as safe (GRAS)), irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the invention can be formulated in accordance with known techniques, see for example, Remington's Pharmaceutical Sciences, Mack Publishing Company, Easton, PA, USA.

The pharmaceutical compositions can be in any form suitable for parenteral, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer-term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use.

The pharmaceutical formulation can be prepared by lyophilising a compound of the invention. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various anti-bacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminium monostearate and gelatin.

In one preferred embodiment of the invention, the pharmaceutical composition is in a form suitable for i.v. administration, for example by injection or infusion. For intravenous or subcutaneous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for subcutaneous (s.c.) administration.

The compound of the invention may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90% (w/w) active ingredient and from 80% (w/w) to 10% of a pharmaceutically acceptable excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g. solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example, tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral or subcutaneous formulations typically contain 0-20% (w/w) buffers, 0-50% (w/w) co-solvents, and/or 0-99% (w/w) Water for Injection (WFI) (depending on dose and if freeze dried). Formulations for intramuscular depots may also contain 0-99% (w/w) oils.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions. One example of a patient pack includes a prefilled syringe. Such pre-filled syringes already contain the drug substance. The front-end portion of a pre-filled syringe to which a needle is to be attached is sealed with a nozzle cap. Prior to injection, the nozzle cap is removed from the front-end portion and a needle is attached thereto. A gasket is then slid by pushing a plunger rod toward the front-end portion so that the drug is expelled.

Compositions for nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compound of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

The active compound will be administered to a patient in need thereof (for example a human or animal patient) in an amount sufficient to achieve the desired therapeutic effect.

Therapeutic Uses

According to a further aspect of the invention, there is provided a compound of formula (I) as defined herein for use in therapy.

According to a further aspect of the invention, there is provided a compound of formula (I) as defined herein for use in the treatment of a disease or disorder mediated and/or caused by an infective agent.

According to a further aspect of the invention, there is provided the use of a compound of formula (I) as defined herein in the manufacture of a medicament for use in the treatment of a disease or disorder mediated and/or caused by an infective agent.

According to a further aspect of the invention, there is provided a method of treating a disease or disorder mediated and/or caused by an infective agent which comprises administering to an individual in need thereof a compound of formula (I) as defined herein.

Examples of infective agents include any pathogen such as a bacteria, fungus, parasite or virus. Thus, in one embodiment, the disease or disorder mediated by and/or caused by an infective agent is bacterial infection.

Examples of such as bacterial infection include infection by the following bacteria: *Staphylococcus* sp. such as *Staphylococcus aureus* (including methicillin resistant *Staphylococcus aureus* (MRSA)), *Clostridia* sp (e.g. *Clostridium difficile*, *Clostridium tetani* and *Clostridium botulinum*), *Enterobacter* species, *Mycobacterium tuberculosis*, *Shigella* sp. such as *Shigella dysenteriae*, *Campylobacter* sp. such as *Campylobacter jejuni*, *Enterococcus* sp. such as *Enterococcus faecalis*, *Bacillus anthracis*, *Yersinia pestis*, *Bordetella pertussis*, Streptococcal species, *Salmonella thyphimurim*, *Salmonella enterica*, *Chlamydia* species, *Treponema pallidum*, *Neisseria gonorrhoeae*, *Borrelia burgdorferi*, *Vibrio cholerae*, *Corynebacterium diphtheriae*, *Helicobacter pylori*, Gram-negative pathogens, such as *Acinetobacter baumannii*, *Pseudomonas aeruginosa*, *Klebsiella pneumoniae*, and *Escherichia coli* (and including strains that are resistant to one or more classes of anti-biotics, especially multi-drug resistant (MDR) strains).

The compound of the invention is generally administered to a subject in need of such administration, for example a human or animal patient, preferably a human.

The compound of the invention will typically be administered in amounts that are therapeutically or prophylactically useful and which generally are non-toxic. However, in certain situations (for example in the case of life threatening diseases), the benefits of administering a compound of the invention may outweigh the disadvantages of any toxic effects or side effects, in which case it may be considered desirable to administer a compound of the invention in amounts that are associated with a degree of toxicity.

The compound of the invention may be administered over a prolonged term (i.e. chronic administration) to maintain beneficial therapeutic effects or may be administered for a short period only (i.e. acute administration). Alternatively, they may be administered in a continuous manner or in a manner that provides intermittent dosing (e.g. a pulsatile manner).

A typical daily dose of the compound of the invention can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the invention can either be administered on a daily basis or on a repeat basis every 2, or 3, or 4, or 5, or 6, or 7, or 10 or 14, or 21, or 28 days for example.

Alternatively, the compound of the invention can be administered by infusion, multiple times per day.

The compound of the invention may be administered in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound of the invention may be administered once or more than once each day. The compound of the invention can be administered continuously (i.e. taken every day without a break for the duration of the treatment regimen). Alternatively, the compound of the invention can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the invention for periods of one hour daily for up to ten days in particular up to five days for one week, and the treatment repeated at a desired interval such as two to four weeks, in particular every three weeks.

More particularly, a patient may be given an infusion of a compound of the invention for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, and in particular a continuous infusion of 24 hours to 72 hours.

Ultimately, however, the quantity of compound of the invention administered and the type of composition used will be commensurate with the nature of the disease or physiological condition being treated and will be at the discretion of the physician.

It will be appreciated that the compound of the invention can be used as a single agent or in combination with other therapeutic agents. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

Where the compound of the invention is administered in combination therapy with one, two, three, four or more other therapeutic agents (preferably one or two, more preferably one), the agents can be administered simultaneously or sequentially. In the latter case, the two or more agents will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the preferred method and order of administration and the respective dosage amounts and regimes for each component of the combination will depend on the particular other medicinal agent and compound of the invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound of the invention and the one or more other therapeutic agent(s) when given as a combination may be determined by the person skilled in the art. Said ratio and the exact dosage and frequency of administration depends on the particular compound of the invention and the other therapeutic agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compound of present invention. A particular weight ratio for the compound of the invention and another therapeutic agent may range from 1/10 to 10/1, more in particular from 1/5 to 5/1, even more in particular from 1/3 to 3/1.

EXAMPLES

The invention will now be illustrated, but not limited, by reference to the specific embodiments described in the following examples. Compounds are named using an automated naming package (ChemDraw) or are as named by the chemical supplier.

The following synthetic procedures are provided for illustration of the methods used; for a given preparation or step the precursor used may not necessarily derive from the individual batch synthesised according to the step in the description given.

Analytical Methods

Wherein examples and preparations cite analytical data, the following analytical methods were used unless otherwise specified:

LCMS

System: LCMS Agilent 1100 (quaternary pump); mass spectrometer: Waters Micromass ZQ Column: Waters XBridge C18 4.6×50 mm, 5 µm.

Solvent: A=water; B=acetonitrile, C=10 mm ammonium formate in water; D=0.05% formic acid in acetonitrile Column temperature: 25° C., injection volume: 5 µL LCMS Method A: 4.5 Minute Acidic Run

| Time (mins) | A (%) | B (%) | C (%) | D (%) | Flow (mL/min) |
| --- | --- | --- | --- | --- | --- |
| 0 | 95 | 0 | 0 | 5 | 2.0 |
| 3.5 | 0 | 95 | 0 | 5 | 2.0 |
| 4.5 | 0 | 95 | 0 | 5 | 2.0 |
| 4.6 | 95 | 0 | 0 | 5 | 2.0 |

LCMS Method B: 4.5 Minute Buffered Run

| Time (mins) | A (%) | B (%) | C (%) | D (%) | Flow (mL/min) |
| --- | --- | --- | --- | --- | --- |
| 0 | 0 | 5 | 95 | 0 | 2.0 |
| 3.5 | 0 | 95 | 5 | 0 | 2.0 |
| 4.5 | 0 | 95 | 5 | 0 | 2.0 |
| 4.6 | 0 | 5 | 95 | 0 | 2.0 |

UPLC (Method C):

Instrumentation: Agilent 1290 Infinity (Binary pump, PDA)

Column: Waters XBridge C18 5 µm 3.0×30 mm (Part no. 186003111)

Conditions:

| Time (mins) | A (%) | B (%) | Flow (mL/min) |
| --- | --- | --- | --- |
| 0 | 95 | 5 | 1.0 |
| 1.0 | 95 | 5 | 1.0 |
| 6.0 | 5 | 95 | 1.0 |
| 7.0 | 5 | 95 | 1.0 |
| 7.1 | 95 | 5 | 1.0 |
| 8.0 | 95 | 5 | 1.0 |

Solvent: A=0.05% TFA in water; B=acetonitrile

Column temperature: 40° C., injection volume: 1-20 µL

UPLC-MS (Method D):

Instrumentation: Waters Acquity UPLC H-Class (Quaternary pump, PDA, ELSD)

Column: Waters Acquity UPLC BEH C18 1.7 µm 2.1×50 mm (Part no. 186002350)

Mass spectrometer: Waters Acquity QDA

Conditions:

| Time (mins) | A (%) | B (%) | C (%) | Flow (mL/min) |
| --- | --- | --- | --- | --- |
| 0 | 93 | 2 | 5 | 0.8 |
| 4.0 | 0 | 95 | 5 | 0.8 |
| 4.6 | 0 | 95 | 5 | 0.8 |

Solvent: A=water; B=acetonitrile, C=2% v/v ammonia (35% v/v) in water

Column temperature: 40° C., injection volume: 0.5 µL

LCMS (Method E):

Instrumentation: Waters Acquity

Column: Waters XBridge C18, 3.5 µm, 2.1×30 mm

Conditions:

| Time (mins) | A (%) | B (%) | Flow (mL/min) |
| --- | --- | --- | --- |
| 0 | 95 | 5 | 1.0 |
| 6.0 | 5 | 95 | 1.0 |
| 7.0 | 5 | 95 | 1.0 |
| 8.0 | 95 | 5 | 1.0 |

Solvent: A=0.1% TFA in water; B=acetonitrile

Column temperature: 40° C.

NMR

NMR details were recorded on a Jeol ECZ 400R using a Royal HFX probe.

MS

Wherein MS data is reported, for large molecular weight compounds a mass-to-charge ratio (m/z) is typically observed.

Abbreviations

Wherein the following abbreviations have been used, the following meanings apply:

Ahx is aminocaproic acid;

aq. is aqueous;

Boc is tert-butyloxycarbonyl;

br s is broad singlet;

$CDCl_3$ is deuterochloroform;

$CD_3OD$ is deuteromethanol;

CTC resin is chlorotrityl chloride resin;
d is doublet;
Dab is 2,4-diaminobutyric acid;
DCM is dichloromethane;
Dde is (1,(4,4-dimethyl-2,6-dioxocyclohex-1-ylidene)-3-ethyl);
DIPEA is diisopropylethylamine;
DMF is dimethylformamide;
DMSO is dimethylsulfoxide;
$d_6$-DMSO is deuterated DMSO;
ES is electrospray ionisation technique;
EtOAc is ethyl acetate;
Fmoc is 9-fluorenylmethoxycarbonyl;
g is gram;
Gly is glycine;
$H_2O$ is water;
HATU is O-(7-azabenzotriazol-1-yl)-N,N,N',N'-tetramethyluronium hexafluorophosphate;
HBTU is O-(benzotriazol-1-yl)-N,N,N',N'-tetramethyluronium hexafluorophosphate;
HCl is hydrochloric acid;
HOBt is hydroxybenzotriazole;
HPLC is high performance liquid chromatography;
$KHCO_3$ is potassium hydrogen carbonate;
L is litre;
LCMS is liquid chromatography mass spectrometry;
Leu is leucine;
m is multiplet;
mg is milligram;
M is molar;
MeCN is acetonitrile;
MeOH is methanol;
$MgSO_4$ is magnesium sulfate;
MHz is megaHertz;
mL is millilitre;
mmol is millimole;
MS is mass spectrometry;
$NaHCO_3$ is sodium hydrogen carbonate;
NaOH is sodium hydroxide;
NaOMe is sodium methoxide;
$NH_3$ is ammonia;
NMR is nuclear magnetic resonance;
Pd/C is palladium on carbon;
$Pd(PPh_3)_4$ is tetrakis(triphenylphosphine)palladium(O);
$Pd(PPh_3)_2Cl_2$ is palladium(II)bis(triphenylphosphine)dichloride
Phe is phenylalanine;
Ppm is parts per million;
$PhSiH_3$ is phenylsilane;
Psi is pounds per square inch;
Rt is retention time;
s is singlet;
t is triplet;
TBTU is O-(benzotriazol-1-yl)-N,N,N',N'-tetramethyluronium tetrafluoroborate;
TEA is triethylamine;
Thr is threonine;
TIS is triisopropylsilane;
TFA is trifluoroacetic acid;
μL is microlitre
UPLC is ultra performance liquid chromatography and
v is volume.

Preparation 1

2-((3'-((Benzyloxy)carbonyl)-[1,1'-biphenyl]-4-yl)oxy)acetic acid

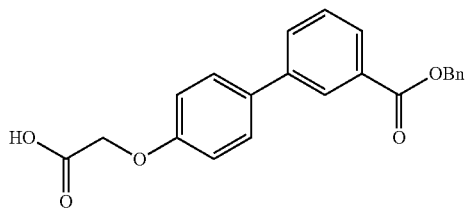 [SMILES: O=C(O)COc1ccc(-c2cccc(C(=O)OCc3ccccc3)c2)cc1]

A solution of benzyl 4'-(2-(tert-butoxy)-2-oxoethoxy)-[1,1'-biphenyl]-3-carboxylate (Preparation 2, 7.80 g, 18.6 mmol) in DCM/TFA/water (10:10:1 v/v/v, 80 mL) was stirred for 2 hours at room temperature. The reaction was concentrated in vacuo, azeotroped with dioxane/toluene (1:1, v/v, 80 mL), triturated with toluene, filtered and dried in a vacuum oven to afford the title compound as a colourless solid (6.11 g, 90%).

LCMS (Method B): Rt=2.43 minutes, $ES^+$ MS m/z 363.2 $[M+H]^+$, theoretical mass: 362.4.

$^1$H NMR (400 MHz, $d_6$-DMSO): δ ppm 13.00 (1H, s), 8.15 (1H, t), 7.95-7.90 (2H, m), 7.65-7.55 (3H, m), 7.50-7.45 (2H, m), 7.45-7.30 (3H, m), 7.05-7.00 (2H, m), 5.40 (2H, s), 4.70 (2H, s).

Preparation 2

Benzyl 4'-(2-(tert-butoxy)-2-oxoethoxy)-[1,1'-biphenyl]-3-carboxylate

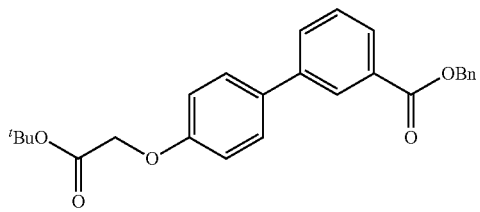 [SMILES: CC(C)(C)OC(=O)COc1ccc(-c2cccc(C(=O)OCc3ccccc3)c2)cc1]

To benzyl 4'-hydroxy-[1,1'-biphenyl]-3-carboxylate (Preparation 3, 15 g, 49.3 mmol) dissolved in DMF (150 mL) was added tert-butyl bromoacetate (10.9 mL, 73.9 mmol) and potassium carbonate (20.4 g, 148 mmol). The resulting suspension was stirred for 16 hours at room temperature under nitrogen. The reaction was concentrated in vacuo, the residue was dissolved in water (150 mL) and extracted with EtOAc (2×150 mL). The combined organic layers were washed with brine (150 mL), NaOH (2M, 150 mL), dried over $MgSO_4$ and concentrated in vacuo. The residue was purified using silica gel column chromatography (Biotage SP1, 340 g silica column, eluting with 5-40% EtOAc/heptane) to afford the title compound as a colourless oil (17.8 g, 86%).

LCMS (Method B): Rt=4.14 minutes, no mass ion observed.

¹H NMR (400 MHz, CDCl₃): δ ppm 8.25 (1H, s), 8.00 (1H, d), 7.70 (1H, d), 7.55 (2H, d), 7.50-7.25 (6H, m), 7.00 (2H, d), 5.40 (2H, s), 4.55 (2H, s), 1.50 (9H, s).

Preparation 3

Benzyl 4'-hydroxy-[1,1'-biphenyl]-3-carboxylate

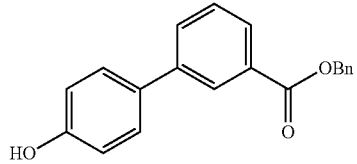 [SMILES: O=C(OCc1ccccc1)c1cccc(-c2ccc(O)cc2)c1]

A mixture of benzyl 3-bromobenzoate (Preparation 4, 15 g, 51.5 mmol), sodium carbonate (19.1 g, 180 mmol) and (4-hydroxyphenyl)boronic acid (8.53 g, 61.8 mmol) dissolved in dioxane/water (5:1 v/v, 450 mL) was deoxygenated for 30 minutes under nitrogen. Pd(PPh₃)₄ (5.95 g, 5.15 mmol) was added and the reaction was heated to 100° C. for 90 minutes under nitrogen. After cooling to room temperature, EtOAc (450 mL) and water (450 mL) were added and the layers were separated. The aqueous layer was extracted with EtOAc (2×450 mL) and the combined organic layers washed with brine (450 mL). The organic layer was dried over MgSO₄ and the solvent removed in vacuo to afford a black residue. The residue was filtered through a pad of silica (1 inch) washing with EtOAc/heptane (1:1 v/v, 2 L) and concentrated in vacuo. The residue was triturated with toluene (75 mL) and filtered. The resulting solid was washed with further toluene (25 mL) and dried under reduced pressure to afford the title compound as a tan solid (12.7 g, 81%).

LCMS (Method B): Rt=3.39 minutes, ES⁻ MS m/z 303.3 [M–H]⁻, theoretical mass: 304.4.

¹H NMR (400 MHz, CDCl₃): δ ppm 8.25 (1H, s), 8.00 (1H, d), 7.70 (1H, d), 7.50-7.30 (8H, m), 6.90 (2H, d), 5.40 (2H, s), 5.00 (1H, br s).

Preparation 4

Benzyl 3-bromobenzoate

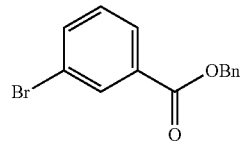 [SMILES: O=C(OCc1ccccc1)c1cccc(Br)c1]

To a solution of 3-bromobenzoic acid (20 g, 99.5 mmol) dissolved in DMF (100 mL) was added KHCO₃ (9.96 g, 99.5 mmol). Benzyl bromide (11.8 mL, 99.5 mmol) was added dropwise and the reaction was stirred at room temperature under nitrogen for 16 hours overnight. The reaction was concentrated in vacuo. The residue which was partitioned between EtOAc (200 mL) and water (200 mL). The layers were separated and the organic layer was washed with citric acid (1M, 200 mL), NaHCO₃ (saturated, aqueous, 200 mL) and brine (200 mL). The organic layer was dried over MgSO₄ and the solvent removed under reduced pressure to afford the title compound as a pale yellow oil (28.3 g, 97%).

LCMS (Method B): Rt=3.80 minutes, no ionisation observed.

¹H NMR (400 MHz, CDCl₃): δ ppm 8.20 (1H, s), 8.00 (1H, s), 7.65 (1H, s), 7.50-7.25 (6H, m), 5.35 (2H, s).

Preparation 5

4'-((2,19-dioxo-22-(((2R,3R,4R,5R,6S)-3,4,5-trihydroxy-6-methyltetrahydro-2H-pyran-2-yl)oxy)-6,9,12,15-tetraoxa-3,18-diazadocosyl)oxy)-[1,1'-biphenyl]-3-carboxylic acid

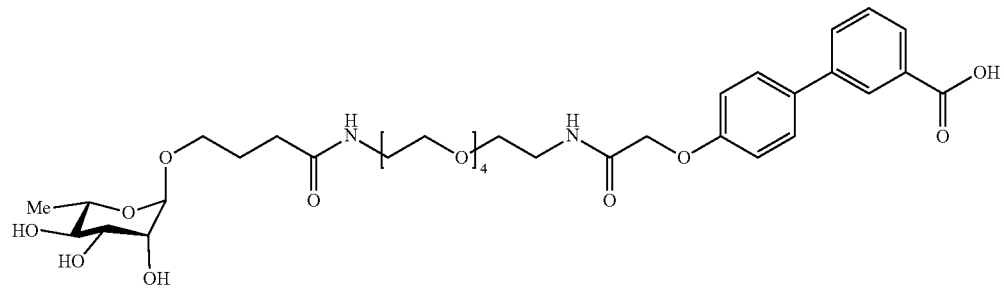

To a solution of (2R,3R,4R,5S,6S)-2-((1-((3'-((benzyloxy)carbonyl)-[1,1'-biphenyl]-4-yl)oxy)-2,19-dioxo-6,9,12,15-tetraoxa-3,18-diazadocosan-22-yl)oxy)-6-methyltetrahydro-2H-pyran-3,4,5-triyl triacetate (Preparation 6, 114 mg, 121 μmol) in MeOH was added NaOMe in MeOH (25% w/v, 157 μL, 726 μmol) and the reaction was stirred at room temperature for 1 hour. The solution was concentrated in vacuo, and the residue purified using reverse phase column chromatography eluting with 5-45% MeCN/water with 0.1% NH₃ to afford the product of both simultaneous removal of acetate and benzyl groups. The resulting residue was freeze dried to afford the title compound as a colourless solid (30 mg, 34%).

LCMS (Method B): Rt=1.64 minutes, ES⁺ MS m/z 723 [M+H]⁺

Preparation 6

(2R,3R,4R,5S,6S)-2-((1-((3'-((benzyloxy)carbonyl)-[1,1'-biphenyl]-4-yl)oxy)-2,19-dioxo-6,9,12,15-tetraoxa-3,18-diazadocosan-22-yl)oxy)-6-methyltetrahydro-2H-pyran-3,4,5-triyl triacetate

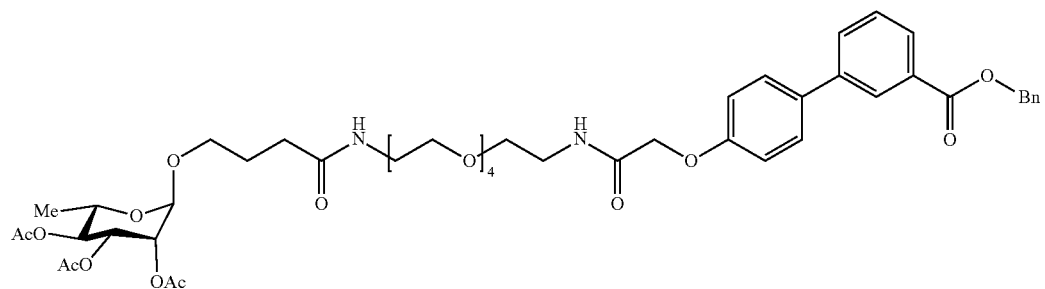

To a solution of 2-((3'-((benzyloxy)carbonyl)-[1,1'-biphenyl]-4-yl)oxy)acetic acid (Preparation 1, 17 mg, 48 μmol) in DCM (0.5 mL) was added triethylamine (21 μL, 150 μmol) and a solution of (2R,3R,4R,5S,6S)-2-((1-amino-16-oxo-3,6,9,12-tetraoxa-15-azanonadecan-19-yl)oxy)-6-methyltetrahydro-2H-pyran-3,4,5-triyl triacetate (Preparation 7, 30 mg, 50 μmol) in DCM (0.5 mL). The reaction was stirred at room temperature for 1 hour. The reaction was concentrated in vacuo, purified using silica gel column chromatography eluting with 0-15% MeOH in DCM and used directly in the next step.

Preparation 7

(2R,3R,4R,5S,6S)-2-((1-amino-16-oxo-3,6,9,12-tetraoxa-15-azanonadecan-19-yl)oxy)-6-methyltetrahydro-2H-pyran-3,4,5-triyltriacetate

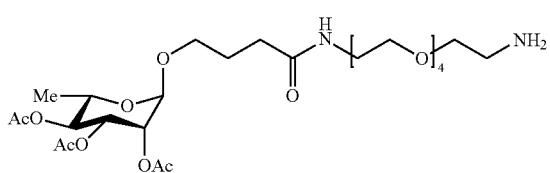

To a solution of (2R,3R,4R,5S,6S)-2-((1-azido-16-oxo-3,6,9,12-tetraoxa-15-azanonadecan-19-yl)oxy)-6-methyltetrahydro-2H-pyran-3,4,5-triyl triacetate (Preparation 8, 477 mg, 768 μmol) in MeOH/water (1:1 v:v, 20 mL) was added 5% Pd/C (50 mg). The reaction was degassed and stirred under a balloon of hydrogen for 3 hours. The reaction was filtered and concentrated in vacuo to afford the title compound as a colourless oil (429 mg, 93%).

UPLC-MS (Method D): Rt=1.94 minutes, ES+ MS m/z 595 [M+H]+

Preparation 8

(2R,3R,4R,5S,6S)-2-((1-azido-16-oxo-3,6,9,12-tetraoxa-15-azanonadecan-19-yl)oxy)-6-methyltetrahydro-2H-pyran-3,4,5-triyltriacetate

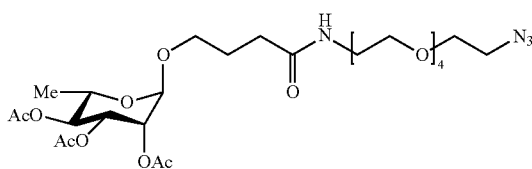

To a solution of (2R,3R,4R,5S,6S)-2-(4-((2,5-dioxopyrrolidin-1-yl)oxy)-4-oxobutoxy)-6-methyltetrahydro-2H-pyran-3,4,5-triyltriacetate (Preparation 9, 473 mg, 1 mmol) in DCM (10 mL) was added a solution of 14-azido-3,6,9,12-tetraoxatetradecan-1-amine (236 mg, 0.9 mmol) in DCM (2 mL). Triethylamine (250 μL) was added and the reaction was stirred at room temperature for 18 hours. The reaction was concentrated in vacuo and purified using reverse phase column chromatography eluting with 3-45% MeCN in water with 0.1% NH$_3$ to afford the title compound as a colourless oil (477 mg, 77%).

UPLC-MS (Method D): Rt=2.21 minutes, ES+ MS m/z 621 [M+H]+

$^1$H NMR (400 MHz, CDCl$_3$): δ ppm 6.40 (1H, m), 5.27-5.23 (1H, m), 5.06 (1H, t), 4.72 (1H, s), 3.90-3.83 (1H, m), 3.81-3.75 (1H, m), 3.70-3.60 (20H, m), 3.51-3.46 (2H, m), 2.46 (2H, t), 2.14 (3H, s), 2.05 (3H, s), 1.99 (3H, s), 2.02-1.96 (2H, m), 1.22 (3H, d).

Preparation 9

(2R,3R,4R,5S,6S)-2-(4-((2,5-dioxopyrrolidin-1-yl)oxy)-4-oxobutoxy)-6-methyltetrahydro-2H-pyran-3,4,5-triyl triacetate

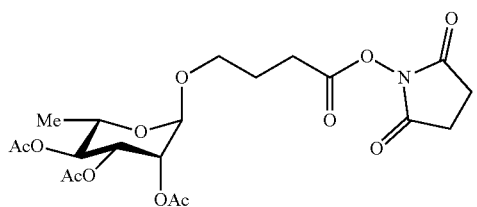

To a solution of 4-(((2R,3R,4R,5S,6S)-3,4,5-triacetoxy-6-methyltetrahydro-2H-pyran-2-yl)oxy)butanoic acid (JACS (2010) 132, 17236-17246, 376 mg, 1 mmol) in DCM (9 mL) was added 1-hydroxypyrrolidine-2,5-dione (230 mg, 2 mmol) followed by 1-ethyl-3-(3-dimethylaminopropyl)carbodiimide (383 mg, 2 mmol). The reaction was stirred at room temperature for 18 hours. The reaction was diluted with DCM (20 mL) and washed with brine/water (2:1 v:v, 30 mL). The organic layer was dried (MgSO$_4$) and concentrated in vacuo to afford the title compound as a clear oil that was used directly in the next step.

$^1$H NMR (400 MHz, CDCl$_3$): δ ppm 5.30 (1H, s), 5.27-5.23 (2H, m), 5.06 (1H, t), 4.74 (1H, s), 3.87-3.78 (2H, m), 3.55-3.50 (1H, m), 2.87-2.81 (4H, m), 2.74 (2H, t), 2.14 (3H, s), 2.08-2.03 (4H, m), 1.98 (3H, s), 1.22 (3H, d).

Preparation 10

4'-(2-oxo-2-((2-(4-(((2R,3R,4R,5R,6S)-3,4,5-trihydroxy-6-methyltetrahydro-2H-pyran-2-yl)oxy)butanamido)ethyl)amino)ethoxy)-[1,1'-biphenyl]-3-carboxylic acid

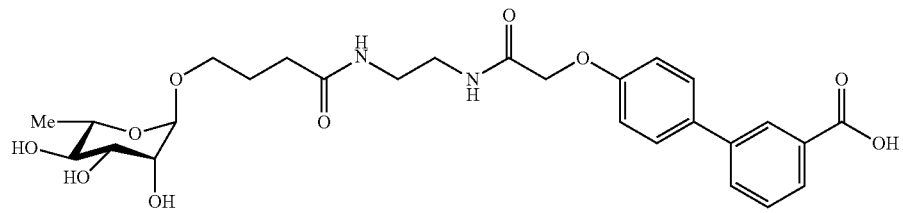

To a solution of 4'-(2-oxo-2-((2-(4-(((2R,3R,4R,5S,6S)-3,4,5-triacetoxy-6-methyltetrahydro-2H-pyran-2-yl)oxy)butanamido)ethyl)amino)ethoxy)-[1,1'-biphenyl]-3-carboxylic acid (Preparation 11, 108 mg, 161 μmol) in MeOH was added NaOMe in MeOH (25% w/v, 140 μL, 644 μmol) and the reaction was stirred at room temperature for 1 hour. The reaction was concentrated in vacuo and purified using reverse phase column chromatography eluting with 3-35% MeCN/water with 0.1% NH$_3$ to afford the title compound as a colourless solid (57.6 mg, 65%).

LCMS (Method B): Rt=1.57 minutes, ES$^-$ MS m/z 545 [M−H]$^-$ $^1$H NMR (400 MHz, CDCl$_3$): δ ppm 8.19 (1H, s), 7.88 (1H, d), 7.63 (3H, d), 7.41 (1H, t), 7.09 (2H, d), 4.62 (1H, s), 4.56, (2H, s), 3.77 (1H, s), 3.63-3.61 (2H, m), 3.40-3.33, (3H, m), 3.30 (2H, s), 2.65 (2H, s), 2.24 (2H, t), 1.88-1.83 (2H, m), 1.23 (3H, d).

Preparation 11

4'-(2-oxo-2-((2-(4-(((2R,3R,4R,5S,6S)-3,4,5-triacetoxy-6-methyltetrahydro-2H-pyran-2-yl)oxy)butanamido)ethyl)amino)ethoxy)-[1,1'-biphenyl]-3-carboxylic acid

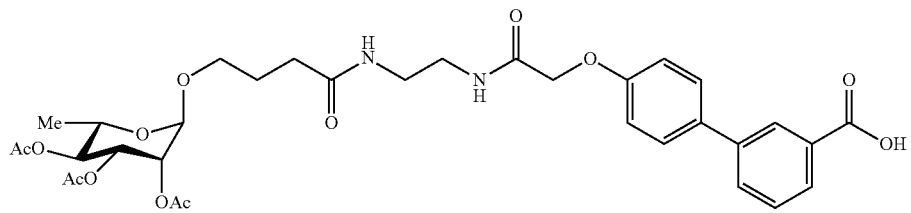

To a solution (2R,3R,4R,5S,6S)-2-(4-((2-(2-((3'-((benzyloxy)carbonyl)-[1,1'-biphenyl]-4-yl)oxy)acetamido)ethyl)amino)-4-oxobutoxy)-6-methyltetrahydro-2H-pyran-3,4,5-triyl triacetate (Preparation 12, 157 mg, 206 μmol) in MeOH/water (1:1 v:v, 15 mL) was added 5% Pd/C (16 mg). The reaction was degassed and stirred under a balloon of hydrogen for 3 hours. The reaction was filtered and concentrated in vacuo to afford the title compound as a clear glass (108 mg, 78%).

LCMS (Method B): Rt=2.17 minutes, ES$^+$ MS m/z 673 [M+H]$^+$ $^1$H NMR (400 MHz, CDCl$_3$): δ ppm 8.25 (1H, s), 8.04 (1H, d), 7.75 (1H, d), 7.57-7.49 (3H, m), 7.36 (2H, br s), 7.02 (2H, d), 6.28 (1H, br s), 5.27-5.20 (2H, m), 5.05 (1H, t), 4.68 (1H, s), 4.55 (2H, s), 3.86-3.82 (1H, m), 3.74-3.68, (1H, m), 3.51-3.40 (5H, m), 2.29 (2H, t), 2.13 (3H, s), 2.03 (3H, s), 2.00 (3H, s), 1.98-1.90 (2H, m), 1.20 (3H, d).

Preparation 12

(2R,3R,4R,5S,6S)-2-(4-((2-(2-((3'-((benzyloxy)carbonyl)-[1,1'-biphenyl]-4-yl)oxy)acetamido)ethyl)amino)-4-oxobutoxy)-6-methyltetrahydro-2H-pyran-3,4,5-triyl triacetate

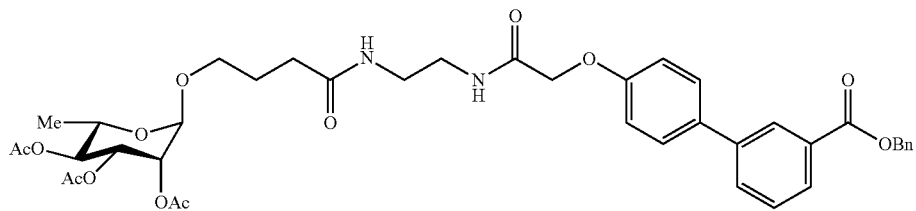

A solution of benzyl 4'-(2-((2-aminoethyl)amino)-2-oxoethoxy)-[1,1'-biphenyl]-3-carboxylate hydrochloride (Preparation 13, 87 mg, 191 µmol) in DCM (2 mL), DMF (0.5 mL) and triethylamine (40 µL) was added to a solution of (2R,3R,4R,5S,6S)-2-(4-((2,5-dioxopyrrolidin-1-yl)oxy)-4-oxobutoxy)-6-methyltetrahydro-2H-pyran-3,4,5-triyl triacetate (Preparation 9, 100 mg, 212 µmol) in DCM (5 mL). The reaction was stirred at room temperature for 18 hours. The reaction was concentrated in vacuo and purified using silica gel column chromatography eluting with 0-5% MeOH in EtOAc to afford the title compound as a clear glass (154 mg, 93%).

LCMS (Method B): Rt=3.33 minutes, ES+ MS m/z 764 [M+H]+

$^1$H NMR (400 MHz, CD$_3$OD): δ ppm 8.23 (1H, s), 8.00 (1H, d), 7.84 (1H, d), 7.62 (2H, d), 7.54 (1H, t), 7.48 (2H, d), 7.42-7.34 (3H, m), 7.11 (2H, d), 5.40 (2H, s), 5.18-5.16 (1H, m), 4.98 (1H, t), 4.69 (1H, s), 4.57 (2H, s), 3.85-3.81 (1H, m), 3.70-3.65, (1H, m), 3.43-3.37 (4H, m), 2.99 (1H, s), 2.86 (1H, s), 2.68 (2H, s), 2.26 (2H, t), 2.10 (3H, s), 2.01 (3H, s), 1.93 (3H, s), 1.88-1.85 (2H, m), 1.14 (3H, d).

Preparation 13

Benzyl 4'-(2-((2-aminoethyl)amino)-2-oxoethoxy)-[1,1'-biphenyl]-3-carboxylate hydrochloride

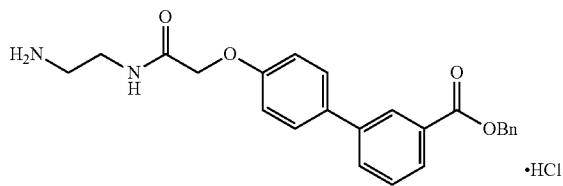 [SMILES: NCCNC(=O)COc1ccc(-c2cccc(C(=O)OCc3ccccc3)c2)cc1 ; Cl]

To a solution of benzyl 4'-(2-((2-((tert-butoxycarbonyl)amino)ethyl)amino)-2-oxoethoxy)-[1,1'-biphenyl]-3-carboxylate (Preparation 14, 1.67 g, 3.31 mmol) in dioxane (50 mL) was added 4M HCl in dioxane (45 mL). The reaction was stirred at room temperature for 2 hours and concentrated in vacuo to afford the title compound as an off-white solid (1.66 g, >100%).

LCMS (Method B): Rt=2.87 minutes, ES+ MS m/z 405 [M+H]+

$^1$H NMR (400 MHz, CD$_3$OD): δ ppm 8.20 (1H, s), 7.95 (1H, d), 7.80 (1H, d), 7.60 (2H, m), 7.52-7.49 (1H, m), 7.46-7.44 (2H, m), 7.40-7.31 (3H, m), 6.99 (2H, d), 5.37 (2H, s), 4.59 (2H, s), 3.60-3.55 (2H, m), 3.12-3.06 (2H, m).

Preparation 14

Benzyl 4'-(2-((2-((tert-butoxycarbonyl)amino)ethyl)amino)-2-oxoethoxy)-[1,1'-biphenyl]-3-carboxylate

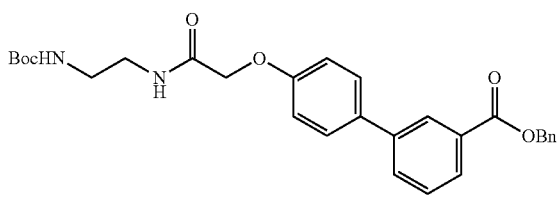 [SMILES: CC(C)(C)OC(=O)NCCNC(=O)COc1ccc(-c2cccc(C(=O)OCc3ccccc3)c2)cc1]

To a solution 2-((3'-((benzyloxy)carbonyl)-[1,1'-biphenyl]-4-yl)oxy)acetic acid (Preparation 1 or WO 2017060729, 1.20 g, 3.31 mmol) and tert-butyl (2-aminoethyl)carbamate (0.82 mL, 4.97 mmol) in DCM/DMF (9:1 v/v, 45 mL) was added triethylamine (1.85 mL, 13.3 mmol) and HATU (1.89 g, 4.97 mmol). The reaction was stirred for 3 hours at room temperature, concentrated in vacuo and purified by silica gel column chromatography eluting with 0-100% EtOAc in heptane, followed by 0-15% MeOH in DCM to afford the title compound as a colourless solid (1.73 g, >100%).

LCMS (Method B): Rt=3.55 minutes, ES+ MS m/z 405 [M-Boc+H]+

$^1$H NMR (400 MHz, CDCl$_3$): δ ppm 8.24 (1H, t), 8.02 (1H, m), 7.73 (1H, m), 7.57-7.54 (2H, m), 7.50-7.44 (3H, m), 7.41-7.34 (3H, m), 7.03-7.00 (2H, m), 5.39 (2H, s), 4.84 (1H, br s), 4.52 (2H, s), 3.49-3.44 (2H, m), 3.34-3.30 (2H, m), 1.41 (9H, s).

Preparation 15

3',5,5'-tris(2-oxo-2-((2-(4-(((2R,3R,4R,5R,6S)-3,4,5-trihydroxy-6-methyltetrahydro-2H-pyran-2-yl)oxy)butanamido)ethyl)amino)ethoxy)-[1,1'-biphenyl]-3-carboxylic acid

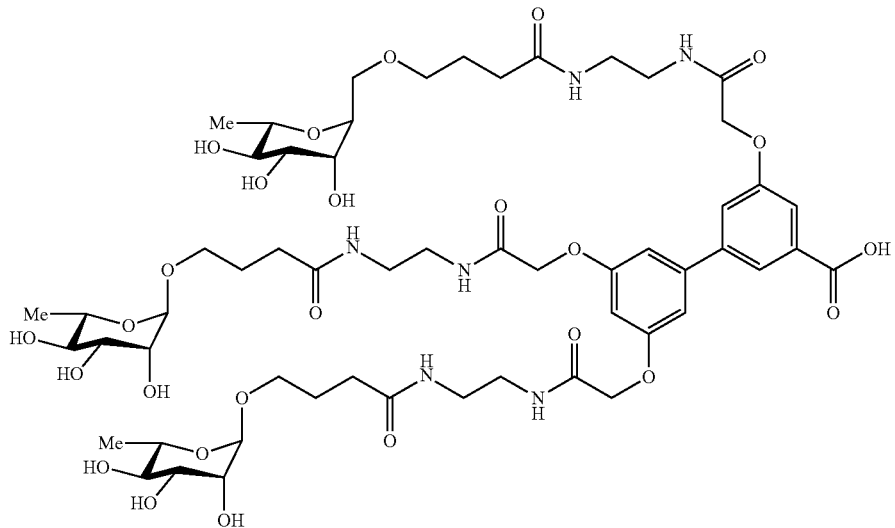

To a solution of 3',5,5'-tris(2-oxo-2-((2-(4-(((2R,3R,4R,5S,6S)-3,4,5-triacetoxy-6-methyltetrahydro-2H-pyran-2-yl)oxy)butanamido)ethyl)amino)ethoxy)-[1,1'-biphenyl]-3-carboxylic acid (Preparation 16, 56 mg, 34.5 μmol) in MeOH was added NaOMe in MeOH (25% w/v, 89 μL, 414 μmol). The reaction was stirred at room temperature for 1 hour. The reaction was concentrated in vacuo and purified using reverse phase chromatography eluting with 3-35% MeCN/water with 0.1% NH₃ to afford the title compound as a colourless solid (28.1 mg, 66%).

LCMS (Method B): Rt=1.37 minutes, ES⁺ MS m/z 1244 [M+H]⁺

Preparation 16

3',5,5'-tris(2-oxo-2-((2-(4-(((2R,3R,4R,5S,6S)-3,4,5-triacetoxy-6-methyltetrahydro-2H-pyran-2-yl)oxy)butanamido)ethyl)amino)ethoxy)-[1,1'-biphenyl]-3-carboxylic acid

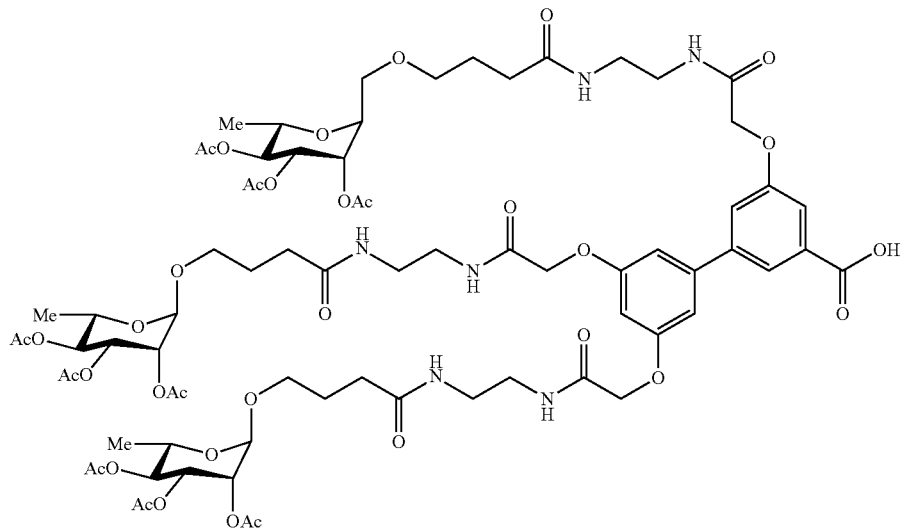

To a solution 3',5,5'-tris(2-oxo-2-((2-(4-(((2R,3R,4R,5S,6S)-3,4,5-triacetoxy-6-methyltetrahydro-2H-pyran-2-yl)oxy)butanamido)ethyl)amino)ethoxy)-[1,1'-biphenyl]-3-carboxylic acid benzyl ester (Preparation 17, 60 mg, 35 μmol) in MeOH/water (1:1 v:v, 10 mL) was added 5% Pd/C (6 mg). The reaction was degassed and stirred under a balloon of hydrogen for 18 hours. The reaction was filtered and concentrated in vacuo to afford the title compound as a clear glass (56 mg, 99%).

LCMS (Method B): Rt=2.46 minutes, ES+ MS m/z 1623 [M+H]+

Preparation 17

3',5,5'-tris(2-oxo-2-((2-(4-(((2R,3R,4R,5S,6S)-3,4,5-triacetoxy-6-methyltetrahydro-2H-pyran-2-yl)oxy)butanamido)ethyl)amino)ethoxy)-[1,1'-biphenyl]-3-carboxylic acid benzyl ester

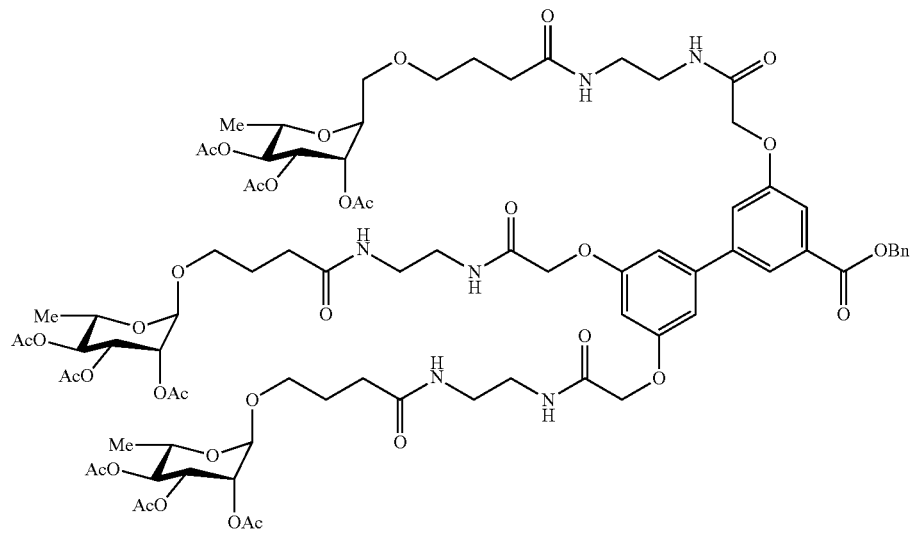

A solution of benzyl 3',5,5'-tris(2-((2-aminoethyl)amino)-2-oxoethoxy)-[1,1'-biphenyl]-3-carboxylate trihydrochloride (Preparation 18, 71.4 mg, 96 μmol) in DCM (2 mL), DMF (0.5 mL) and triethylamine (55 μL) was added to a solution of (2R,3R,4R,5S,6S)-2-(4-((2,5-dioxopyrrolidin-1-yl)oxy)-4-oxobutoxy)-6-methyltetrahydro-2H-pyran-3,4,5-triyl triacetate (Preparation 9, 181 mg, 382 μmol) in DCM (10 mL). The reaction was stirred at room temperature for 18 hours. The reaction was concentrated in vacuo and purified using silica gel column chromatography eluting with 0-15% MeOH in DCM to afford the title compound as a clear glass (60 mg, 37%).

LCMS (Method B): Rt=3.05 minutes, ES+ MS m/z 1713 [M+H]+

Preparation 18

Benzyl 3',5,5'-tris(2-((2-aminoethyl)amino)-2-oxoethoxy)-[1,1'-biphenyl]-3-carboxylate trihydrochloride

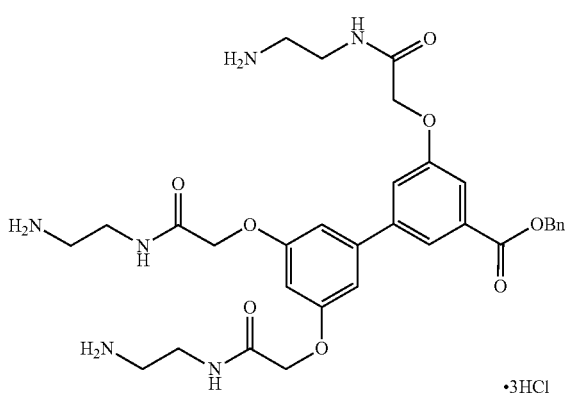 [SMILES: NCCNC(=O)COc1cc(OCC(=O)NCCN)cc(-c2cc(OCC(=O)NCCN)cc(C(=O)OCc3ccccc3)c2)c1]

The title compound was prepared using the method described for Preparation 12 using 2,2',2''-((5'-((benzyloxy)carbonyl)-[1,1'-biphenyl]-3,3',5-triyl)tris(oxy))triacetic acid (WO2017060729) and tert-butyl (2-aminoethyl)carbamate.

LCMS (Method B): Rt=1.76 minutes, ES+ MS m/z 637 [M+H]+

$^1$H NMR (400 MHz, DMSO-$d_6$): δ ppm 8.58-8.41 (3H, m), 8.22-7.98 (9H, m), 7.82 (1H, d), 7.63-7.55 (2H, m), 7.52-7.30 (5H, m), 6.96 (2H, d), 6.73 (1H, d), 5.38 (2H, s), 4.70 (2H, s), 4.60 (4H, s), 3.59-3.40 (6H, m), 2.97-2.81 (6H, m).

Synthesis of Peptide Intermediates

Peptide scaffolds were constructed according to standard Solid Phase Peptide Synthesis (SPPS) using appropriately protected amino acids and CTC resin. The scaffolds were cyclised at an appropriate place in the synthesis. All protected amino acids and linker starting materials are commercially available or prepared according to the references cited herein.

Purification Conditions for Preparative HPLC of Scaffolds:
    Dissolution solvent: water/MeCN
Instrument: Gilson GX-215
    Mobile phase A: 0.075% TFA in water
    Mobile phase B: MeCN
    Gradient: see individual experimental
    Column: Luna 25×200 mm, C18 10 µm, 110 Å+Gemini 150×30 mm, C18 5 µm, 110 Å
    Flow rate: 20 mL/min
    Wavelength: 220/254 nm
    Room temperature Analytical HPLC:

Instrumentation: Agilent 1200

Column: Gemini-NX C18 5 µm, 110 Å, 150×4.6 mm
Conditions:

| Time (mins) | A (%) | B (%) | Flow (mL/min) |
|---|---|---|---|
| 0 | 50 | 50 | 1.0 |
| 20 | 20 | 80 | 1.0 |
| 20.1 | 10 | 90 | 1.0 |
| 23 | 10 | 90 | 1.0 |

Solvent: A=0.1% TFA in water; B=0.1% TFA in acetonitrile

Column temperature: 50° C.

LCMS:

Instrumentation: Agilent 1200 HPLC & 6410 triple quad

Column: Waters XBridge C18, 3.5 µm, 2.1×30 mm

MS: ESI Positive, MS2 scan, 325° C.

Conditions:

| Time (mins) | A (%) | B (%) | Flow (mL/min) |
|---|---|---|---|
| 0 | 90 | 10 | 1.0 |
| 0.9 | 20 | 80 | 1.0 |
| 1.5 | 10 | 90 | 1.0 |
| 1.51 | 10 | 90 | 1.0 |
| 2 | 10 | 90 | 1.0 |

Solvent: A=0.1% TFA in water; B=0.1% TFA in acetonitrile

Column temperature: 30° C.

Preparation 19 (Scaffold 1)

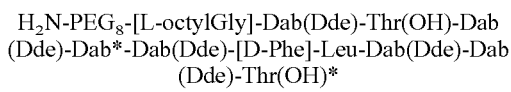

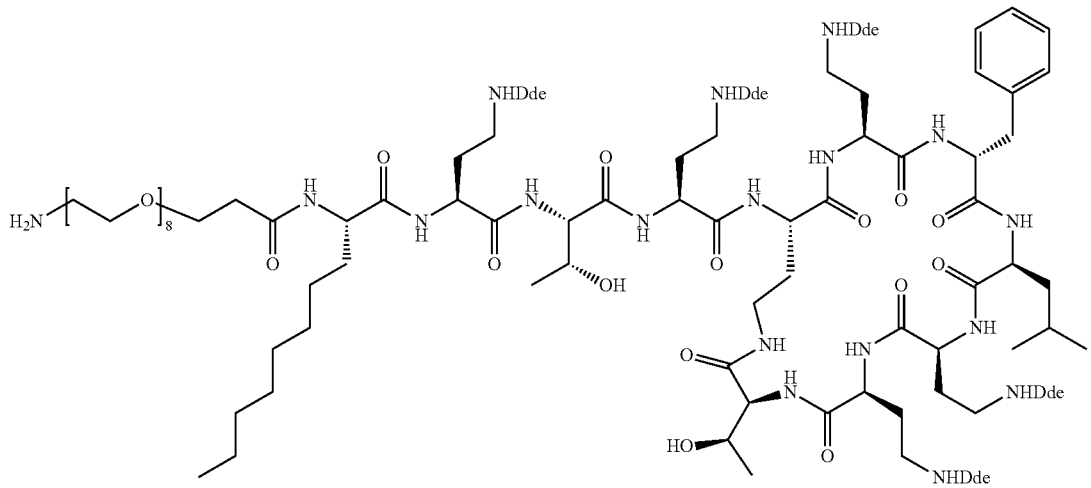

The peptide chain was elongated on CTC resin commencing with Fmoc-Dab(Dde)-OH [to CTC Resin (2 mmol, 2 g, 1.0 mmol/g) and Fmoc-Dab(Dde)-OH (1.08 g, 2 mmol, 1.0 eq) in DCM (30 mL), was added DIPEA (4 eq) and the reaction was mixed for 2 hours. MeOH (2 mL) was added and the reaction was capped and mixed for 30 minutes]. 20% piperidine in DMF was used for de-blocking and the desired amino acid sequence was constructed using HATU (2.85 eq) and DIPEA (6 eq) in DMF (10 mL) to afford Boc(PEG$_8$)-[L-octylGly]-Dab(Dde)-Thr(OtBu)-Dab(Dde)-Dab(Alloc)-Dab(Dde)-[D-Phe]-Leu-Dab(Dde)-O-CTC-resin. At this point the resin was treated with Pd(PPh$_3$)$_2$Cl$_2$ (0.1 eq) and PhSiH$_3$ (10 eq) in DCM followed by resin washing with DMF and MeOH to effect alloc deprotection and dried under nitrogen overnight. The peptide was further elongated as above with the required remaining amino acids. The peptide was treated with 1% TFA/DCM (2×20 mL) for 2 minutes and adjusted to pH=7 with DIPEA and diluted with DCM. TBTU (2 eq) and HOBt (2 eq) were added followed by DIPEA (2 eq), and the mixture was stirred for 1 hour to effect cyclisation. The reaction was washed with 5% aqueous HCl and concentrated in vacuo to afford Boc-(PEG$_8$)-[L-octylGly]-Dab(Dde)-Thr(OH)-Dab(Dde)-Dab*-Dab(Dde)-[D-Phe]-Leu-Dab(Dde)-Dab(Dde)-Thr(OH)*. The crude peptide was treated with 95% TFA/2.5% H$_2$O/2.5% TIS (5 mL) at room temperature and stirred for 30 minutes. The reaction was precipitated with cold isopropyl ether (300 mL) and centrifuged (3 min at 3000 rpm). The crude peptide was washed with isopropyl ether (2×100 mL), centrifuged, and purified using preparative HPLC (Mobile phase A: 0.1% TFA in MeCN, B: H$_2$O) followed by lyophilisation to afford the title compound.

Rt=10.6-11.9 minutes, ES$^+$ MS m/z 1239.2 [M+2H]/2 and 826.4 [M+3H]/3; theoretical mass: 2477

Preparation 20 (Scaffold 2)

Nonanamide-Dab(Ahx-Ahx-NH$_2$)-Thr(OH)-Dab(Dde)-Dab*-Dab(Dde)-[D-Phe]-Leu-Dab(Dde)-Dab(Dde)-Thr(OH)*

HATU (2.85 eq) and DIPEA (6 eq) in DMF (2 mL) to afford nonanamideDab(Dde)-Thr(OtBu)-Dab(Boc)-Dab(Alloc)-Dab(Dde)-[D-Phe]-Leu-Dab(Dde)-O-CTC-resin. At this point the resin was treated with Pd(PPh$_3$)$_2$Cl$_2$ (0.1 eq) and PhSiH$_3$ (10 eq) in DCM followed by resin washing with DMF and MeOH to effect alloc deprotection and dried under nitrogen overnight. The peptide was further elongated as above with the required remaining amino acids. The peptide was cleaved from the resin with 1% TFA/DCM (2×5 mL) for 2 minutes and adjusted to pH=7 with DIPEA in DCM. TBTU (2 eq) and HOBt (2 eq) were added followed by DIPEA (2 eq), and the mixture was stirred for 1 hour to effect cyclisation. The reaction was washed with 5% aqueous HCl and concentrated in vacuo to afford NonanamideDab(Dde)-Thr(OH)-Dab(Boc)-Dab*-Dab(Dde)-[D-Phe]-Leu-Dab(Dde)-Dab(Dde)-Thr(OH)*. The crude peptide was treated with 95% TFA/2.5% H2O/2.5% TIS (5 mL) at room temperature and stirred for 30 minutes. The reaction was precipitated with cold isopropyl ether (50 mL) and centrifuged (3 min at 3000 rpm). The crude peptide was washed with isopropyl ether (2×50 mL), centrifuged, and purified using Preparative HPLC (Mobile phase A: 0.1% TFA in H$_2$O, B: H$_2$O) followed by lyophilisation to afford the scaffold without the linker. To a solution of the peptide in DCM, was added Boc-Ahx-Ahx-OH (1.2 eq) and HBTU (1.2 eq) followed by DIPEA (2 eq) and the reaction was

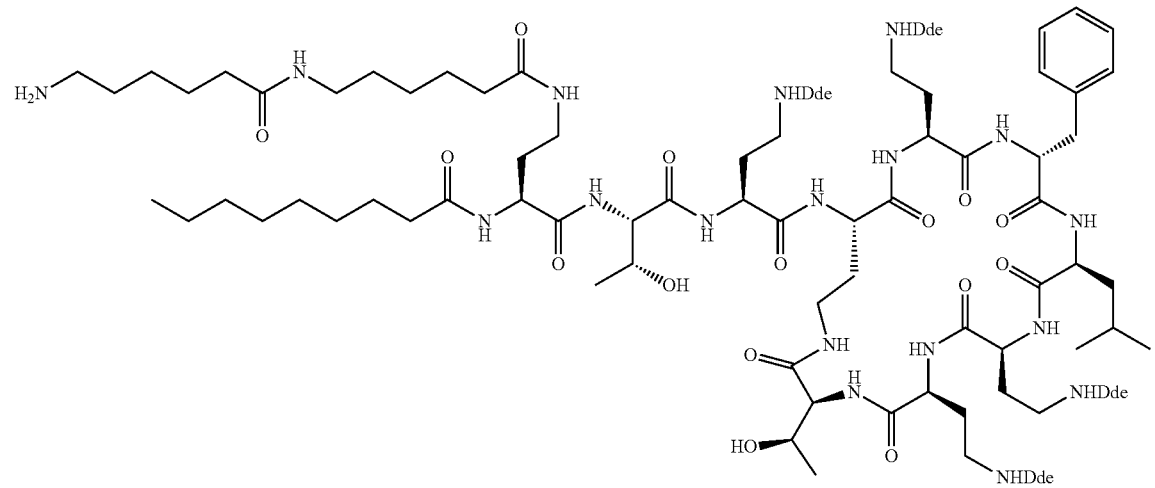

The peptide chain was elongated on CTC resin commencing with Fmoc-Thr(OtBu)-OH [to CTC Resin (0.5 mmol, 0.5 g, 1.0 mmol/g) and Fmoc-Thr(OtBu)-OH (200 mg, 0.5 mmol, 1 eq) in DCM (5.0 mL), was added DIPEA (4 eq) and the reaction was mixed for 2 hours. MeOH (0.5 mL) was added and the reaction was capped and mixed for 30 minutes]. 20% piperidine in DMF was used for de-blocking and the desired amino acid sequence was constructed using stirred for 30 minutes at room temperature. The reaction was washed twice with 5% HCl (aq) and concentrated in vacuo. The residue was treated with 20% TFA/DCM for 20 minutes and concentrated in vacuo. The residue was purified using preparative HPLC (Mobile phase A: 0.1% TFA in H$_2$O, B: H$_2$O) and lyophilised to afford the title compound.

Rt=8.2-9.3 minutes, ES+ MS m/z 1043.7 [M+2H]/2 and 696.3 [M+3H]/3; theoretical mass: 2086.6

Preparation 21 (Dde-Scaffold 3)

H₂N-Ahx-Ahx-[L-octylgly]-Dab(Dde)-Thr(OH)-Dab(Dde)-Dab*-Dab(Dde)-[D-Phe]-Leu-Dab(Dde)-Dab(Dde)-Thr(OH)*

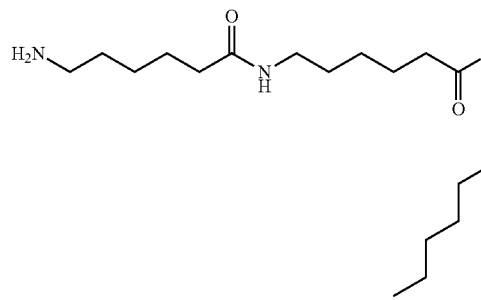

The title compound may be prepared according to Preparation 19 using Fmoc-Dab(Dde)-CTC resin as a starting point together with Boc-Ahx-Ahx-OH and Fmoc-[L-octylGly]-OH. Rt=11.9-12.9 minutes, ES+ MS m/z 1140.2 [M+2H]/2 and 760.7 [M+3H]/3; theoretical mass: 2279.9

Preparation 22 (Boc-Scaffold 3)

H₂N-Ahx-Ahx-[L-octylgly]-Dab(Boc)-Thr(OH)-Dab(Boc)-Dab*-Dab(Boc)-[D-Phe]-Leu-Dab(Boc)-Dab(Boc)-Thr(OH)*

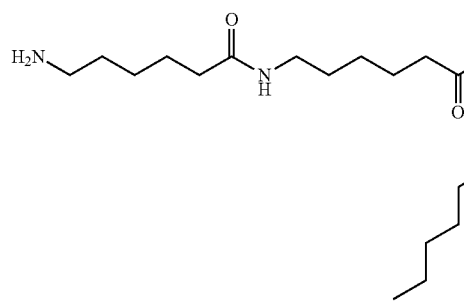

The peptide chain was elongated on CTC resin commencing with Fmoc-Dab(Boc)-O-CTC-Resin.

20% piperidine in DMF (for de-blocking) was added with mixing for 30 minutes. The reaction was drained and washed with DMF (×5). Construction of the desired peptide sequence was continued using HATU (1.9-2.85 eq) and DIPEA (4-6.0 eq) in DMF (10 mL) followed by 20% piperidine in DMF for each amino acid to afford H₂N-Ahx-Ahx-[L-octylGly]-Dab(Boc)-Thr(OH)-Dab(Boc)-Dab(Dde)-Dab(Boc)-[D-Phe]-Leu-Dab(Boc)-O-CTC-resin. The peptide was then treated with a mixture of DCM and DIPEA (4 eq) with Cbz-Cl (2 eq). At this point the resin was treated with 3% hydrazine hydrate in DMF to effect Dde deprotection. The resin was washed with DMF (×5) and the peptide

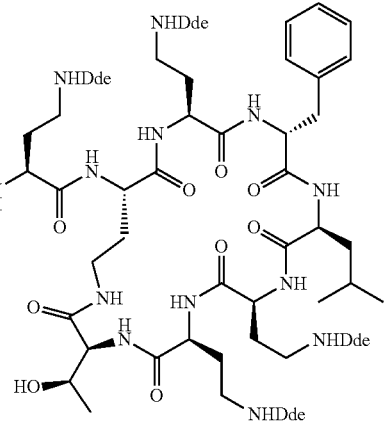

was further elongated as above with the required remaining amino acids. The peptide was treated with 1% TFA/DCM (2×50 mL) for 2 minutes and adjusted to pH=7 with DIPEA and diluted with DCM. TBTU (2 eq) and HOBt (2 eq) were added followed by DIPEA (2 eq), and the mixture was stirred for 1 hour to effect cyclisation. The reaction was washed with 5% aqueous HCl and concentrated in vacuo to afford Cbz-Abx-Abx-[L-octylGly]-Dab(Boc)-Thr(OH)-Dab(Boc)-Dab*-Dab(Boc)-[D-Phe]-Leu-Dab(Boc)-Dab(Boc)-Thr(OH)*.

The crude peptide was treated with 4:1 DMF:MeOH (50 mL) and Pd(OH)₂/C (50%, 2 g) was added under nitrogen.

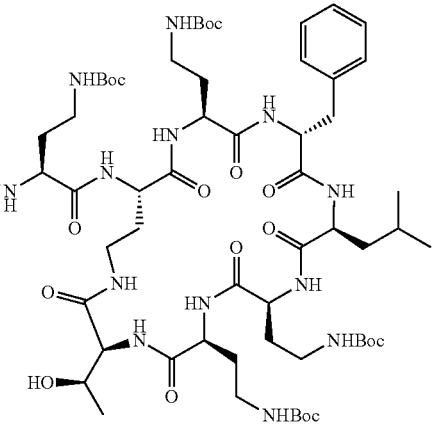

The suspension was purged with hydrogen several times and stirred under 15 psi hydrogen for 4 hours at 35° C. The crude peptide was purified using preparative HPLC as described above using a gradient of between 30-70% MeCN in water (with 0.075% TFA) over 60 minutes to afford the title compound.

HPLC Rt=9.54 minutes, ES⁺ MS m/z 980 [M+2H]/2 and 930 [M-Boc+2H]/2; theoretical mass: 1958

Examples 1-6

Examples 1-5 were prepared in accordance with the following General Method 1:

General Method 1

To a mixture of Linker-Intermediate-$CO_2H$ (1 eq) and Scaffold-$NH_2$ (1.5 eq) in DMF (1 mL) was added HATU (1 eq) and DIPEA (4 eq). The reaction was stirred at room temperature for 1 hour. The reaction was purified directly using reverse phase chromatography eluting with 0-70% MeCN in water and dried under vacuum to afford a white solid. The compound was dissolved in 3% hydrazine hydrate in MeOH (3 mL) and the reaction shaken for 30 minutes. The reaction was concentrated in vacuo and purified using preparative HPLC (Gilson GX-215; column: Luna 25×200 mm, C18 10 μm, 110 Å+Gemini 150×30 mm, C18, 5 μm, 110 Å; eluting with 10-40% MeCN in 0.075% TFA in water at room temperature; flow rate: 20 mL/min) and lyophilised to afford the desired compound.

Example 1

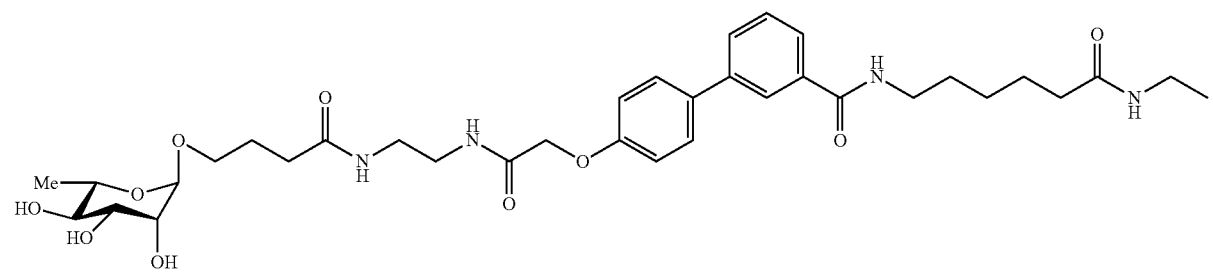

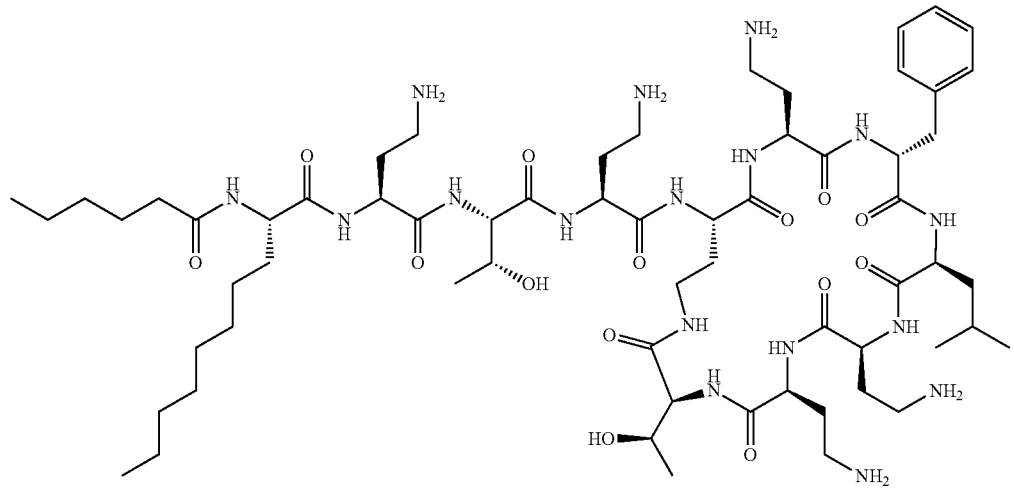

Prepared using Preparation 21 and Preparation 10 according to General Method 1.

$ES^+$ MS m/z (Method E): 994 [M+2H]/2; 663 [M+3H]/3; theoretical mass: 1986

LCMS (Method E): Rt=3.06 minutes

Example 2
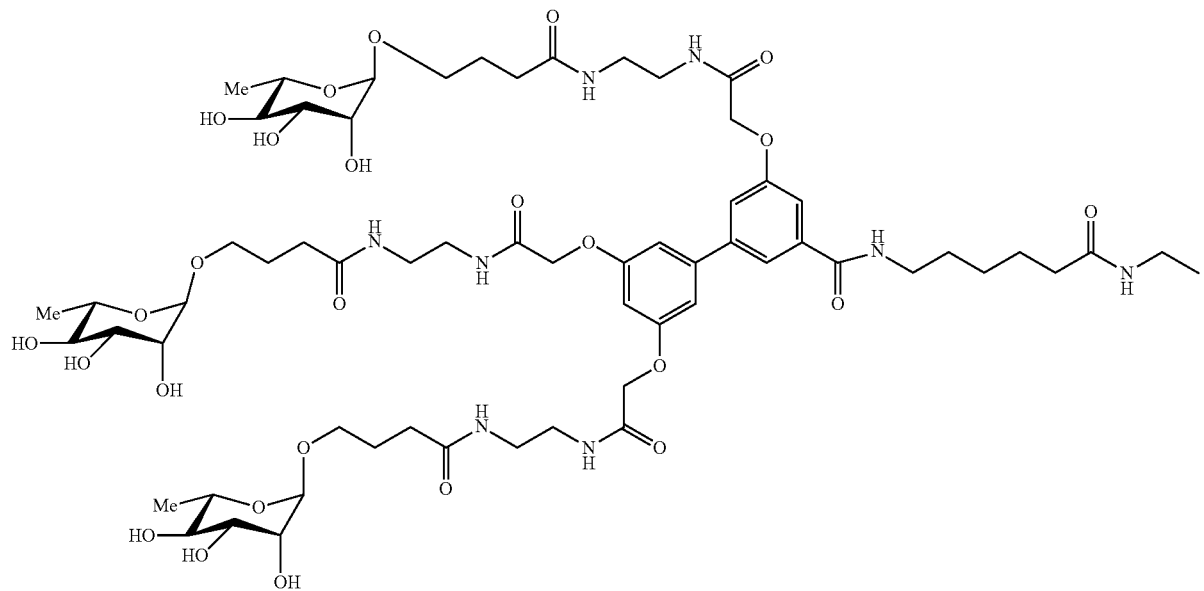
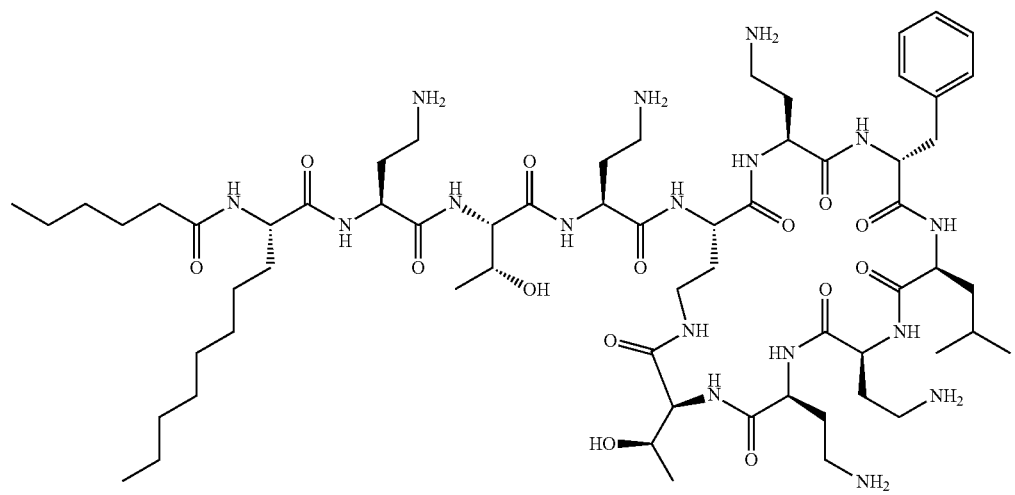
Prepared using Preparation 21 and Preparation 15 according to General Method 1.
ES⁺ MS m/z (Method E): 1342 [M+2H]/2; 895 [M+3H]/3; theoretical mass: 2683
LCMS (Method E): Rt=2.76 minutes Example 3
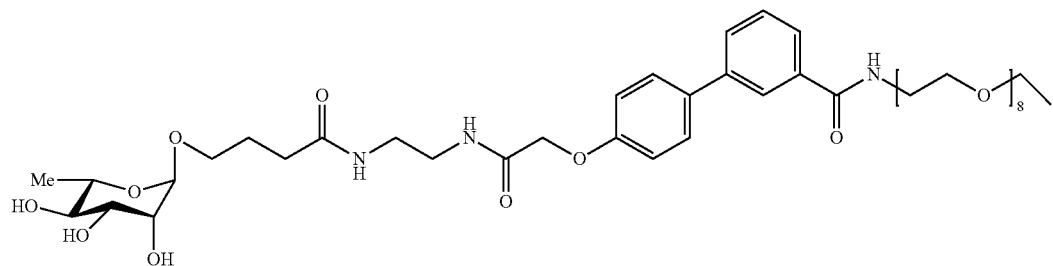
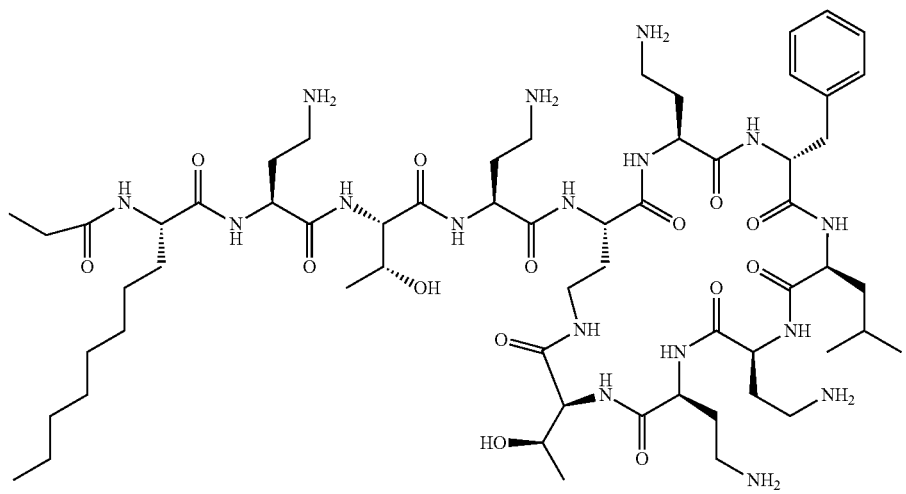
Prepared using Preparation 19 and Preparation 1 according to General Method 1.
ES+ MS m/z (Method E): 1093 [M+2H]/2; 729 [M+3H]/3; theoretical mass: 2183
LCMS (Method E): Rt=3.05 minutes Example 4
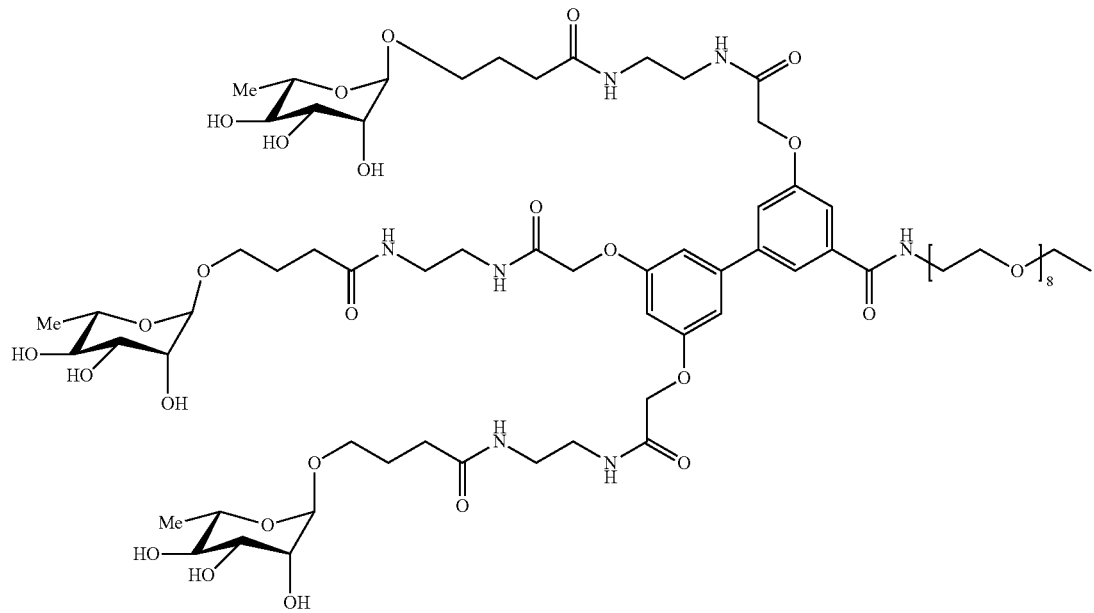
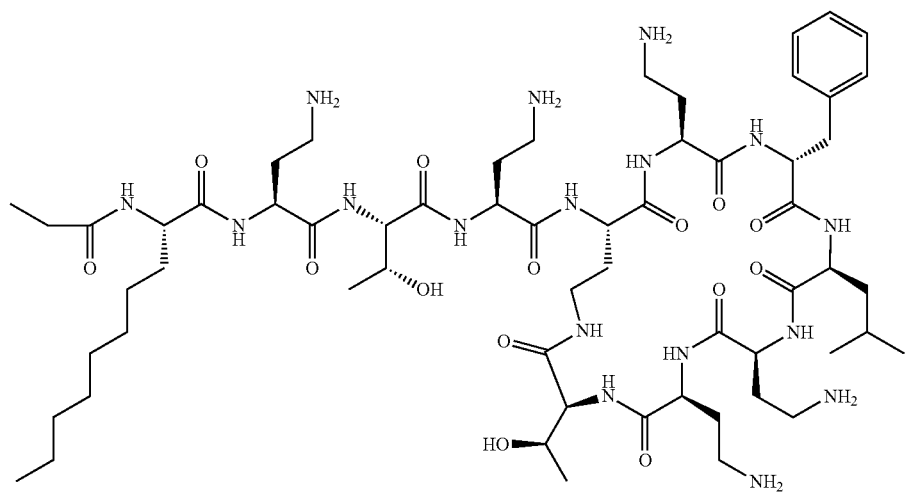
Prepared using Preparation 19 and Preparation 15 according to General Method 1.
ES⁺ MS m/z (Method E): 962 [M+3H]/3; theoretical mass: 2883
LCMS (Method E): Rt=2.76 minutes Example 5
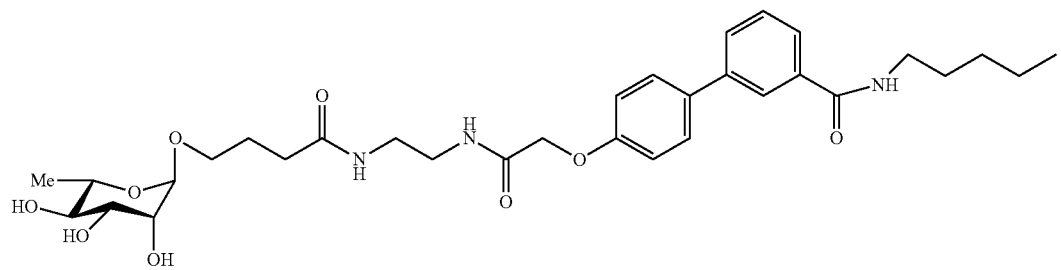
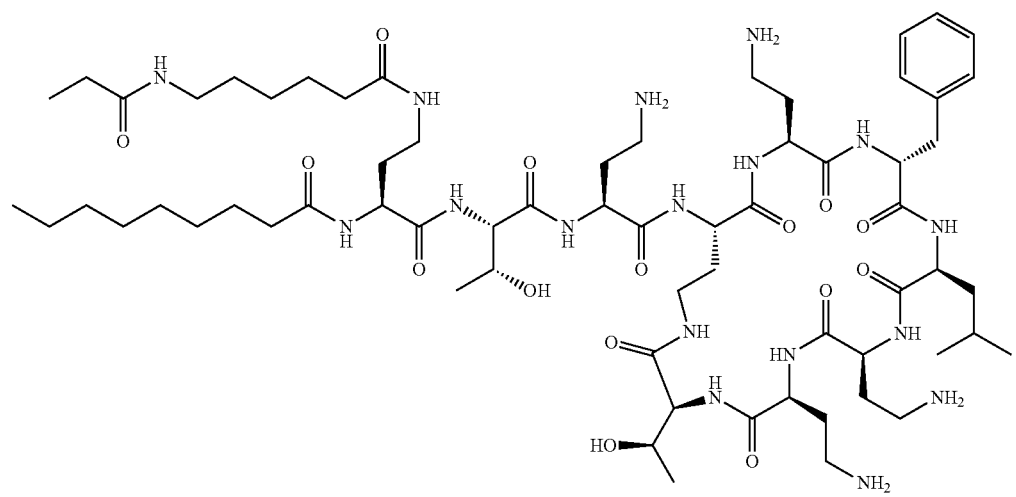
Prepared using Preparation 20 and Preparation 10 according to General Method 1.
ES+ MS m/z (Method E): 979 [M+2]/2; theoretical mass: 1956
LCMS (Method E): Rt=3.08 minutes
Example 6
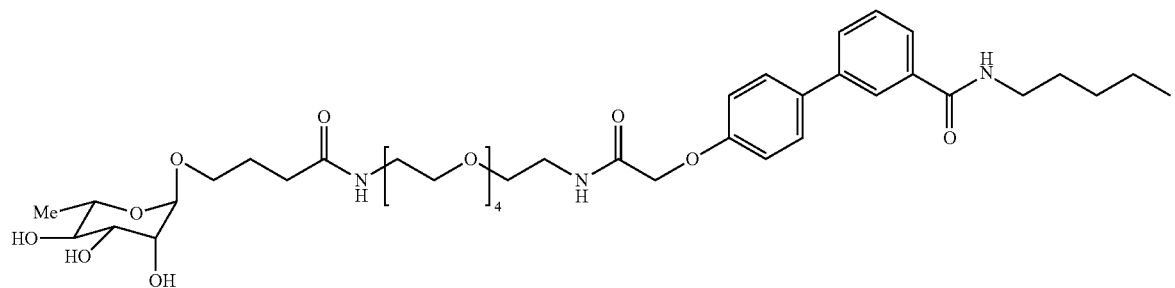

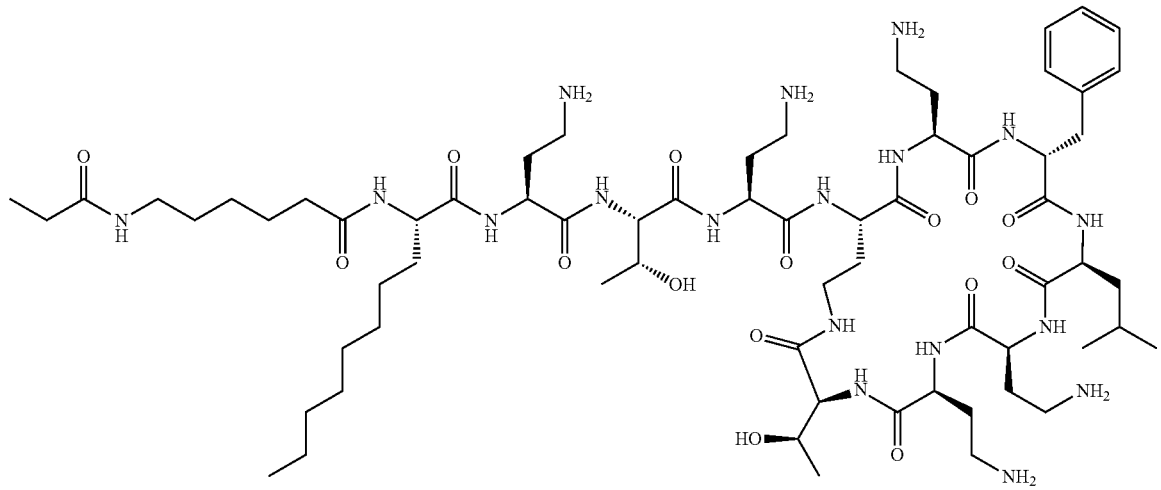

Example 6 was prepared in accordance with the following General Method 2:

General Method 2

To a solution of 4'-((2,19-dioxo-22-(((2R,3R,4R,5R,6S)-3,4,5-trihydroxy-6-methyltetrahydro-2H-pyran-2-yl)oxy)-6,9,12,15-tetraoxa-3,18-diazadocosyl)oxy)-[1,1'-biphenyl]-3-carboxylic acid (Preparation 5, 12 mg, 17 μmol) and triethylamine (3 drops) in DMF (0.5 mL) was added Preparation 22 (27 mg, 13 μmol) in DMF (0.5 mL) followed by HATU (6.8 mg, 18 μmol). The reaction was stirred at room temperature for 15 hours. The reaction was concentrated in vacuo and purified using reverse phase column chromatography eluting with 5-90% MeCN in water to afford the desired boc protected intermediate (10.5 mg, 30%).

LCMS (Method B) Rt=3.24 minutes; ES+ MS m/z 1333.1 [M+2H]/2; theoretical mass: 2664.2.

The intermediate was dissolved in DCM:TFA (3:2, v/v, 2 mL) and stirred at room temperature for 5 minutes. The reaction was quenched into ice-cold TBME (8 mL) and concentrated in vacuo. The residue was purified using reverse phase column chromatography eluting with 3-50% MeCN in water with 0.1% TFA to afford the title compound as white solid (7 mg, 65%).

UPLC (Method C): Rt=2.76 minutes; ES+ MS m/z 1082.6 [M+2H]/2; theoretical mass: 2163.6.

Reference Examples 7-11

Reference Examples 7-11 may be prepared in an analogous manner to the processes described hereinbefore for Examples 1-6.

Reference Example 7

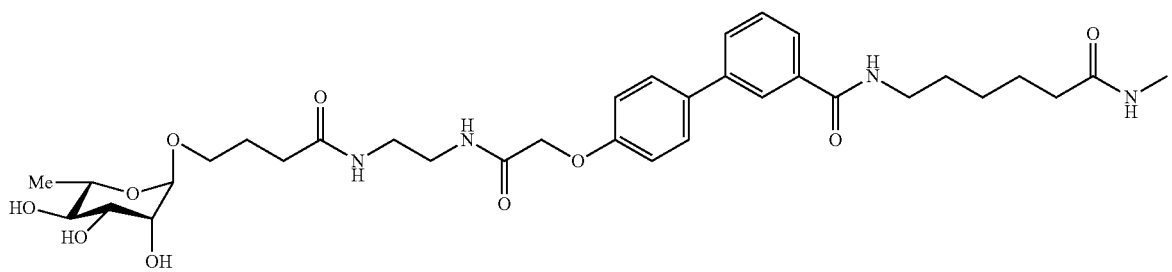

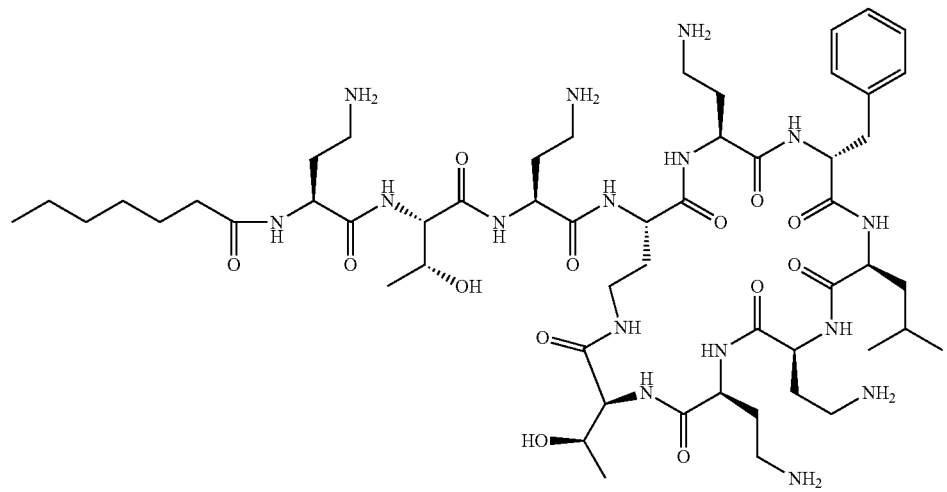
Reference Example 8
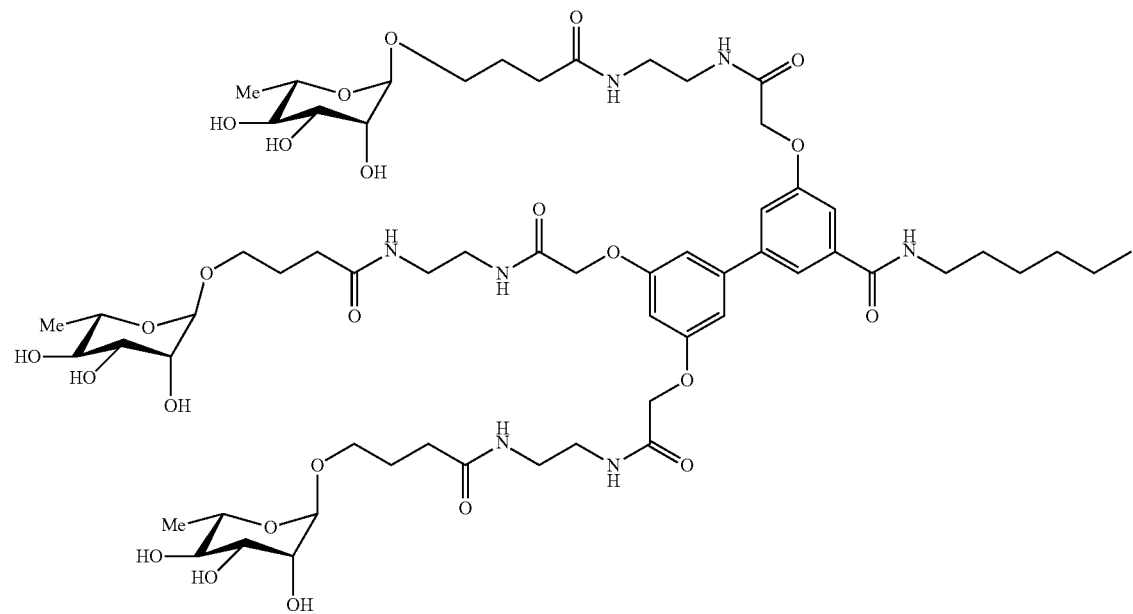

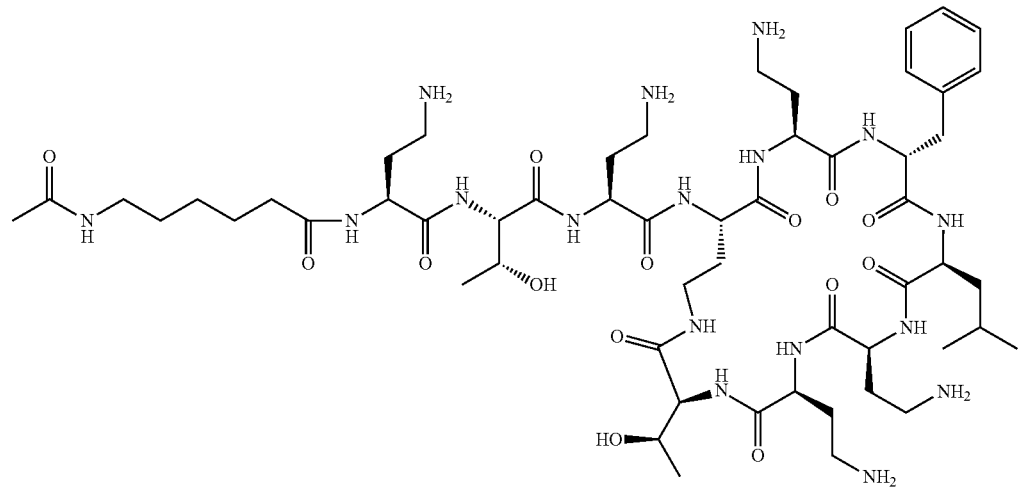
Reference Example 9
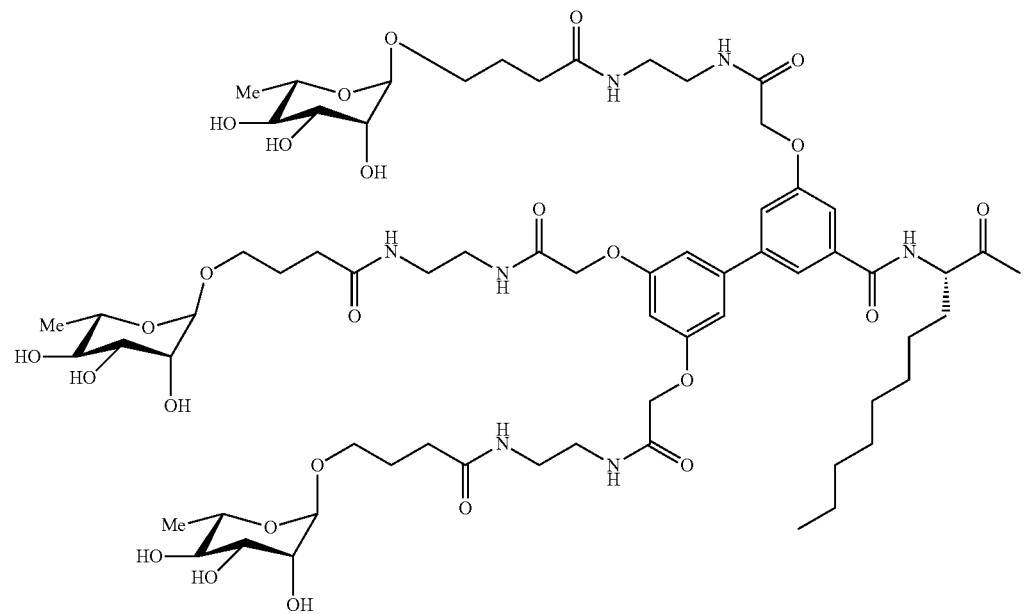

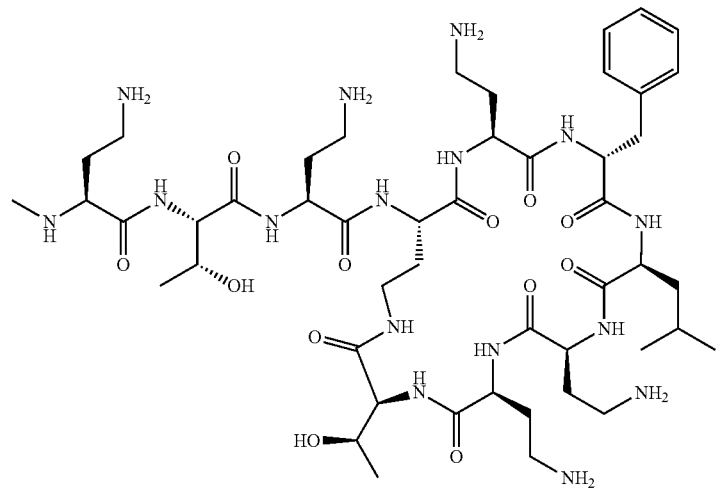
Reference Example 10
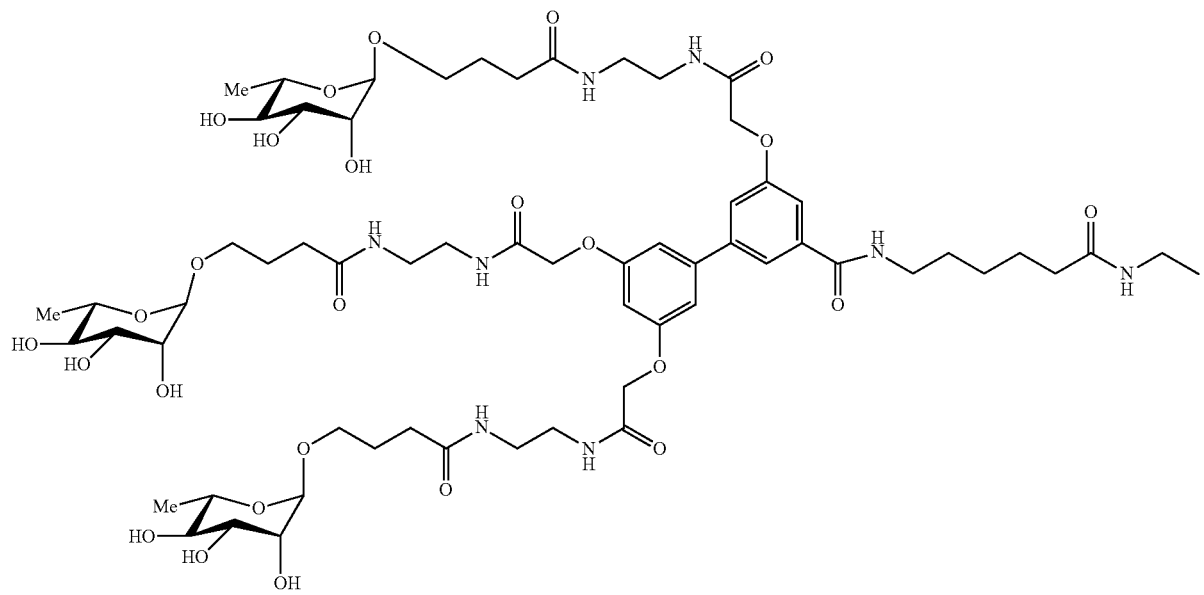

-continued

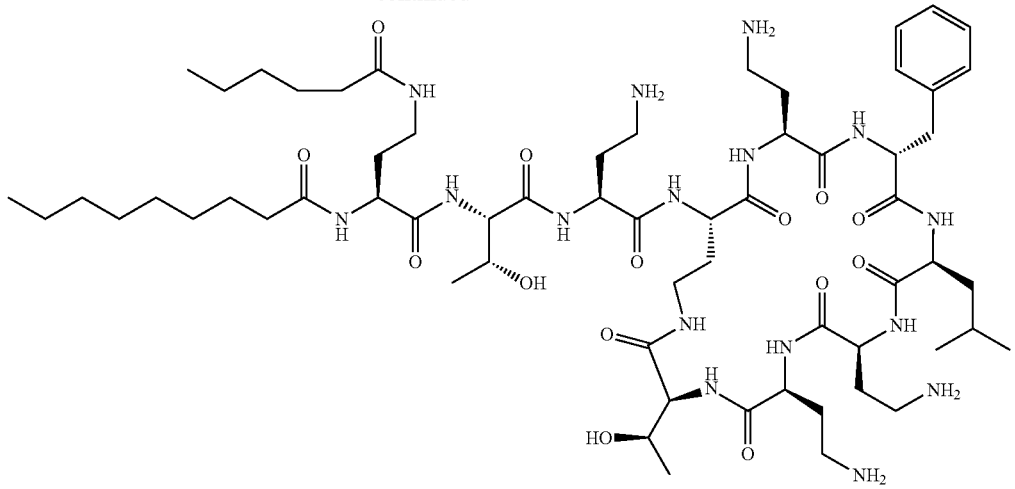

Reference Example 11

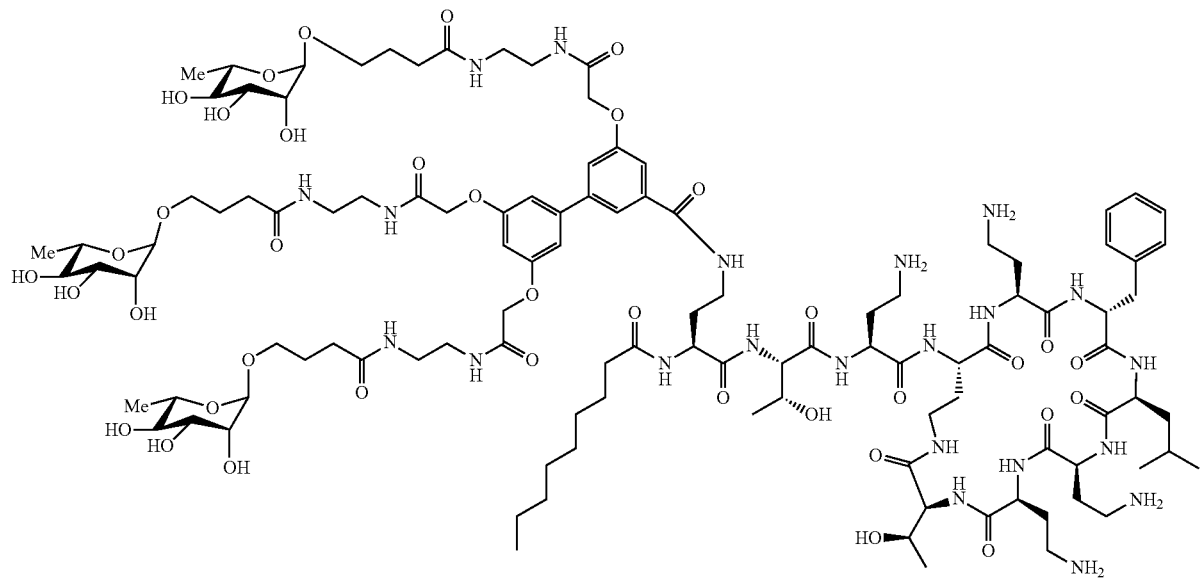

Biological Assays

Flow cytometric antibody recruitment assay using an anti-Rhamnose antibody

Flow cytometry was used to demonstrate binding of L (as a cationic anti-microbial peptide selected from scaffolds 1-3) to *Pseudomonas aeruginosa* bacteria and the interaction of F (the Rhamnose carbohydrate moiety of the anti-microbial peptides) with anti-Rhamnose IgG polyclonal antibodies. A secondary fluorescently labelled anti-IgG antibody was used to detect the anti-Rhamnose antibody binding.

Method

The assays were carried out in polystyrene 96-well U bottom plates (Costar) blocked with 200 μl of Casein blocking buffer for 1 hour at room temperature (Fisher 37528). *Pseudomonas aeruginosa* PA01 (ATCC 15692) was grown in LB broth, Miller (Fisher BP1426-500) to late exponential phase. Subsequently, the bacteria were washed once with Hank's Balanced Salt Solution with calcium and magnesium (HBSS+/+) and then resuspended in HBSS+/+ at a bacterial density of $2 \times 10^9$ colony forming units (CFU)/mL. $1 \times 10^8$ CFU were then incubated for 45 minutes with Example 1-6 compounds (see Table 1) at 0.625 to 40 μM end concentration (Note, due to limited reagent, Example 1 was tested only at 40 μM), 40 μM Polymyxin B, or buffer alone (vehicle control), at room temperature and shaking at 450 rpm. The bacteria were then washed three times with 200 μL HBSS+/+, prior to adding 50 μL of the human anti Rhamnose IgG polyclonal antibody at a final concentration of 42 μg/mL in HBSS+/+. The samples were incubated for 1 hour at room temperature shaking at 450 rpm. The bacteria were washed three times as above, prior to adding 100 μL of a PE-labeled anti-human IgG Fc secondary antibody (Biolegend 409304) at 10 μg/mL in HBSS+/+ and incubating at room temperature for 1 hour at 450 rpm. After three final washes with 200 μL HBSS+/+, the bacteria were resuspended in 200 μL HBSS+/+ and evaluated for anti-Rhamnose antibody binding on a Cytoflex flow cytometer (Beckman Coulter). 50,000 counts of bacterial particles were sampled and the median fluorescent shift was recorded in the PE-A channel. Data from all samples were analysed using Kaluza software (Beckman Coulter). All samples were run in technical duplicates and biological experiments repeated as indicated in the table.

Table 1 and FIG. 1 demonstrate the binding of anti-Rhamnose IgG antibodies to the surface of the bacteria in the presence and absence of the respective compounds using the flow cytometry assay described above. The fold shift over background was calculated by dividing the Median Fluorescent Intensity (MFI) obtained in the presence of 40 μM of the Example compounds by the MFI value obtained in the vehicle controls, i.e., the absence of Examples. The higher the fold shift over background, the more anti-Rhamnose was bound to the bacterial surface. The shift in fluorescence intensity (PE) occurs due to the binding event at each end of the molecule.

TABLE 1

| Example No | IgG Recruitment (40 μM, Average fold change) | Experiments |
|---|---|---|
| Example 1 | 77.7 | N = 1 |
| Example 3 | 49.85 | N = 2 |
| Example 5 | 8.45 | N = 2 |
| Example 2 | 3.4 | N = 2 |
| Example 4 | 2.9 | N = 2 |
| Example 6 | 332.6 | N = 1 |
| Polymyxin B (40 μM) | 1.58 | N = 2 |

Flow Cytometric Complement Deposition Assay with Human Serum

The assays were carried out in polystyrene 96-well U bottom plates (Costar). E. coli K1:O18ac:H7 (American Type Culture Collection, ATCC 700973) was grown in LB broth, Miller (Fisher BP1426-500) to late exponential phase. Subsequently, the bacteria were washed in Hank's Balanced Salt Solution with calcium and magnesium (HBSS+/+) and then resuspended in assay buffer, i.e., PBS with 1% bovine serum albumin (BSA, Sigma A2153) at a concentration of $2\times10^9$ CFU/mL. $1\times10^8$ CFU were then incubated with 5 μM of Examples 1-6 (see Table 2), 20 μM PmxB or assay buffer alone, at 4° C. for 45 min in a total volume of 50 μL. Subsequently, 150 μL ice-cold HBSS+/+ was added, the bacteria were pelleted and then washed once with 200 μL HBSS+/+, prior to adding 100 μL of pooled human serum (Innovate Research IPLA-CSER) as anti-Rhamnose antibody and complement source in PBS, 1% BSA to a final serum concentration of 25%. Bacteria were incubated at 37° C. for 20 min to allow for anti-Rhamnose binding to the compounds and complement deposition. 100 μL ice-cold HBSS+/+ was added to each well to stop the reaction. The bacteria were pelleted by centrifugation at 4° C. and the supernatants discarded. The bacteria were then washed two times with 200 μL refrigerated HBSS+/+, prior to adding 100 μL of APC-labelled anti-human C3b/iC3b antibody (Biolegend 846106; clone 3E7/C3b) at 1:25 dilution in PBS, 1% BSA and incubated at 4° C. for 45 min. After three final washes with 200 μL HBSS+/+, the bacteria were resuspended in HBSS+/+ and their fluorescence profile as an indicator for complement deposition evaluated on a Cytoflex flow cytometer (Beckman Coulter). The median fluorescent intensity (MFI) was recorded in the APC channels. Data from all samples were analysed using Kaluza software (Beckman Coulter). All samples were run in technical duplicates and biological experiment repeated as indicated in the table.

Figure 2:
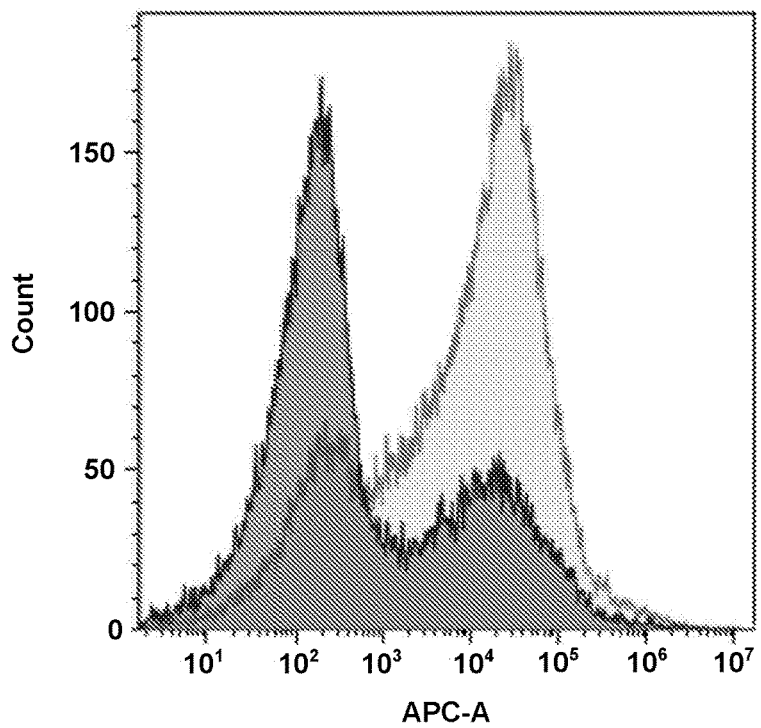
FIG. 2: Deposition of C3b/iC3b from human serum to the surface of the bacteria using the flow cytometry assay described herein.
Figure 2:
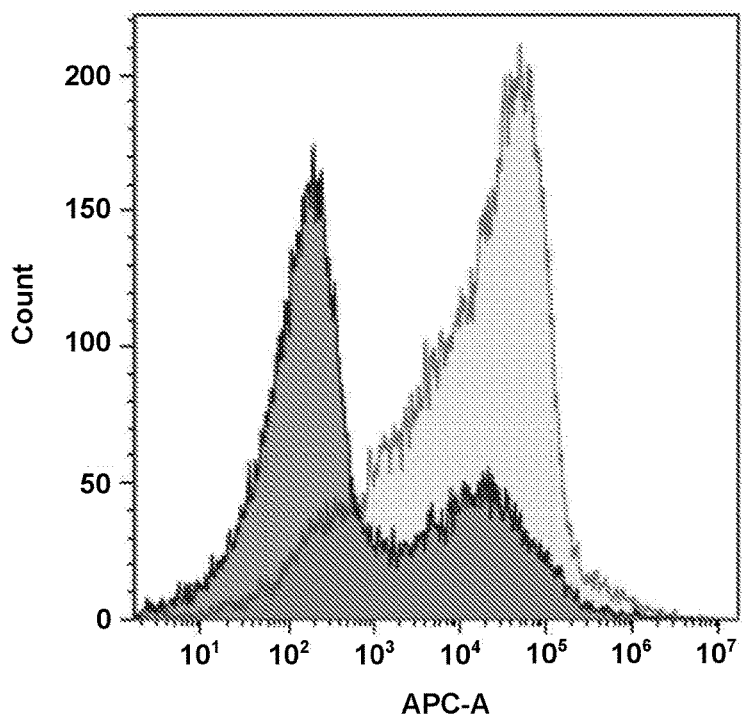

Table 2 and FIG. 2 demonstrate the deposition of C3b/iC3b from human serum to the surface of the bacteria using the flow cytometry assay described above. The fold shift over background was calculated by dividing the MFI obtained in the presence of the Examples (5 μM) by the MFI obtained in the absence of Examples, i.e., in the presence of vehicle. The shift in fluorescence intensity (APC) occurred due to detection of covalently bound complement components C3b/iC3b to the surface of the bacteria.

TABLE 2

| Example No | C3b deposition (5 μM, Average fold change) | Experiments |
|---|---|---|
| Example 1 | 109.8 | N = 2 |
| Example 3 | 114.0 | N = 2 |
| Example 5 | 20.5 | N = 2 |
| Example 2 | 148.1 | N = 2 |
| Example 4 | 38.0 | N = 2 |
| Example 6 | 183.95 | N = 2 |
| PmxB 20 μM | 24.535 | N = 1 |

The invention claimed is:
1. A process for preparing a compound of formula (I):

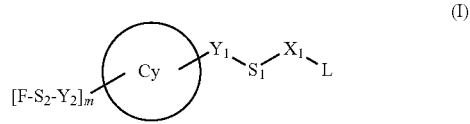

wherein:
L represents a binding moiety which is a cationic antimicrobial peptide linked to $X_1$ by an amine;
$S_1$ represents a bond or a spacer selected from a —$(CH_2)_a$— or —$(CH_2)_b$—$(CH_2$—$CH_2$—$O)_c$—$(CH_2)_d$— group, wherein one or two of said —$CH_2$— groups may optionally be substituted by a —C(O)NH— or —NHC(O)— group;
a represents an integer selected from 2 to 13;
b represents an integer selected from 0 to 3;
c represents an integer selected from 1 to 10;
d represents an integer selected from 1 to 3;
$S_2$ represents a spacer selected from a —$(CH_2)_e$— or —$(CH_2)_f$—$(CH_2$—$CH_2$—$O)_g$—$(CH_2)_h$— group, wherein one or two of said —$CH_2$— groups may optionally be substituted by a —C(O)NH— or —NHC(O)— group;
e represents an integer selected from 1 to 10;
f represents an integer selected from 2 to 6;
g represents an integer selected from 1 to 5;
h represents an integer selected from 1 to 5;
$X_1$ represents a bond or —C(O)—
$Y_1$ and $Y_2$ independently represent a bond, —O—, —S—, —NH—, —C(O)—, —NHC(O)— or —C(O)NH— group;
F represents Rhamnose;
m represents an integer selected from 1 to 5; and
Cy represents biphenyl, such that said —$Y_1$—$S_1$—$X_1$-L group may be present on either of said phenyl rings and said [F—$S_2$—$Y_2$]$_m$— group or groups may be present on either of said phenyl rings which comprises:

(a) preparing the compound of formula (IA) by reacting a compound of formula (II) with a compound of formula (III) followed by a suitable deprotection step:

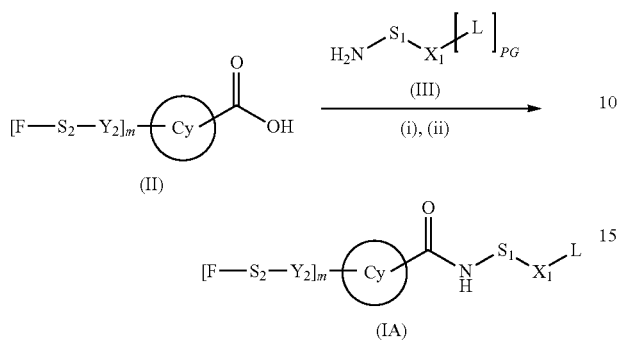

wherein $S_2$, $Y_2$, m, Cy, $S_1$, $X_1$, L and F are as defined in the compound of formula (I) and PG is a suitable peptide protecting group selected from Dde or tertbutoxycarbonyl (Boc); or (b) preparing the compound of formula (IB) by reacting a compound of formula (IV) with a compound of formula (V) followed by a suitable deprotection step:

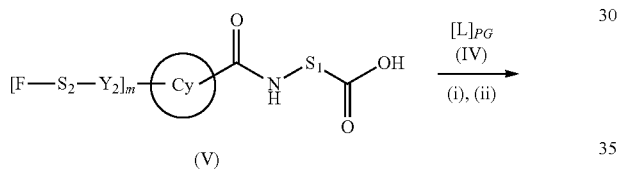

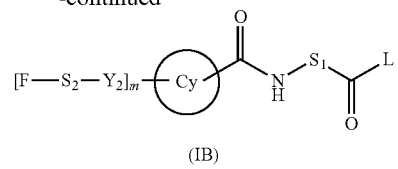

wherein $S_2$, $Y_2$, m, Cy, $S_1$, $X_1$, L and F are as defined in the compound of formula (I) and PG is a suitable peptide protecting group selected from Dde or tertbutoxycarbonyl (Boc); or (c) preparing a compound of formula (I) by reacting a compound of formula (VI) with a compound of formula (VII) followed by a suitable deprotection step:

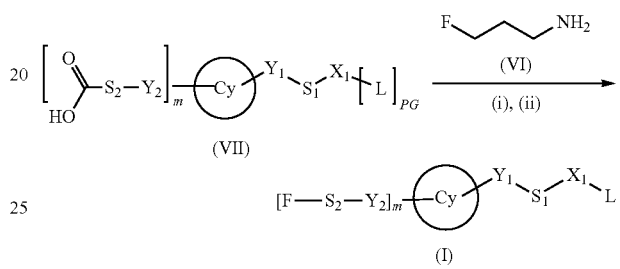

wherein $S_2$, $Y_2$, m, Cy, $S_1$, $X_1$, L and F are as defined in the compound of formula (I) and PG is a suitable peptide protecting group selected from Dde or tertbutoxycarbonyl (Boc); or (d) interconversion of a compound of formula (I), or protected derivative thereof, into an alternative compound of formula (I), or protected derivative thereof.

* * * * *